United States Patent [19]
Briles et al.

[11] Patent Number: 5,955,089
[45] Date of Patent: Sep. 21, 1999

[54] STRAIN SELECTION OF PNEUMOCOCCAL SURFACE PROTEINS

[75] Inventors: David E. Briles; Susan Hollingshead, both of Birmingham, Ala.; Robert Becker, Henryville, Pa.

[73] Assignee: UAB Research Foundation, Birmingham, Ala.

[21] Appl. No.: 08/710,749

[22] Filed: Sep. 20, 1996

Related U.S. Application Data

[63] Continuation-in-part of application No. 08/465,746, Jun. 6, 1995, Pat. No. 5,679,768, which is a continuation of application No. 08/048,896, Apr. 20, 1993, abandoned.

[51] Int. Cl.⁶ .................. A61K 39/09; G01N 33/569; C07K 1/00; C07H 21/04

[52] U.S. Cl. .................. 424/244.1; 424/93.44; 424/165.1; 424/237.1; 435/7.34; 530/350; 536/23.7

[58] Field of Search .................. 424/165.1, 237.1, 424/244.1, 93.44; 435/7.34; 530/350; 536/23.7

[56] References Cited

PUBLICATIONS

McDaniel et al, "Localization of protection–eliciting epitopes on PspA of Streptococcus pneumoniae between amino acid residues 192 and 260", Microbial Pathogenesis, 17:323–337, Nov. 1, 1994.

*Primary Examiner*—James C. Housel
*Assistant Examiner*—Rodney P. Swartz
*Attorney, Agent, or Firm*—Frommer Lawrence & Haug LLP; William S. Frommer; Thomas J. Kowalski

[57] ABSTRACT

The present invention relates to vaccine composition(s) comprising at least two PspAs from strains selected from at least one family, the family being defined by PspAs from strains belonging to the family having greater than or equal to 50% homology in aligned sequences of a C-terminal region of an alpha helical region of PspA. Additionally, the families are further comprised of clades, wherein PspAs from strains which belong to a clade exhibit at least 75% sequence homology in aligned sequences of the C-terminal region of the alpha helix of PspA. Vaccine compositions of the present invention preferably comprise a minimum of 4 and a maximum of 6 strains representing a single clade each, and the at least two PspAs are optionally serologically or broadly cross-reactive.

40 Claims, 10 Drawing Sheets

```
Ac122a     ........    ........    ..LDKEAG   EAELDKKADG  LPNKVSDLEK  EISNLEILLG
Ef3296a    LAKKQTELEK  LLDSLDPEGK  TQDELDKEAE  EAELDKKADE  LPNKVADLEK  EISNLEILLG
Bg8090a    LAKKQTELEK  LLDNLDPEGK  TQDELDKEAA  EAELDKKADE  LPNKVADLEK  EISNLEILLG
Consensus  LAKKQTELEK  LLD-LDPEGK  TQDELDKEA-  EAELDKKADE  LPNKVADLEK  EISNLEILLG Ac122a     GADSEDDTAA  LPNKLATKKA  ELEKTQKELD  AALNELGPDG  DEEE
Ef3296a    GADSEDDTAA  LPNKLATKKA  ELEKTQKELD  AALNELGPDG  DEEE
Bg8090a    GADPEDDTAA  LPNKLATKKA  ESEKTPKELD  AALNELGPDG  DEEE
Consensus  GADSEDDTAA  LPNKLATKKA  ELEKTQKELD  AALNELGPDG  DEEE
```

FIG. 5

```
Bg11703a    LEKAEAELEN  LLSTLDPEGK  TQDELDKEAA  EAELNKKVEA  LPNQV SELEE  ELSKLEDNLK 60
Bg7817a     LEKAGAGLGN  LLSTLDPEGK  TQDELDKEAA  EAELNKKVEA  LPNQVAELEE  ELSKLEDNLK 60
Ef5668a     LEDAAELELEK  LLSTLDPPEGK  TQDELDKEAA  EAELNEKVEA  LQNQVAELEE  ELSKLEDNLK 60
Bg7561a     LEKAGAGLGN  VLATLDPPEGK  TQDELDKGAA  EAELNKKVEA  LPNPVXELEE  ELSPPEDNLK 60
Consensus   LEKAGAGLGN  LLSTLDPGGK  TQDELDKEAA  EAELNKKVEA  LPNQV-ELEE  ELSKLEDNLK 60

Bg11703a    DAETNNVEDY  IKEGLEEAIA  TKQAELEKTP  KELDAALNEL  GPDGDEEE  108
Bg7817a     DAETNHVEDY  IKEGLEEAIA  TKQAELEKTP  KELDAALNEL  GPDGDEEE  108
Ef5668a     DAETNNVEDY  IKEGLEEAIA  TKKAELEKTQ  KELDAALNEL  GPDGDEEE  108
Bg7561a     DAETNHVEDY  IKEGLEEAIA  TKQAELEETP  QEVDAALNDL  VPDGGEEE  108
Consensus   DAETN-VEDY  IKEGLEEAIA  TKQAELEKTP  KELDAALNEL  GPDGDEEE  108
```

FIG.6

Clade 5

ATCC6303  LEDSGLGLEK  VLATLDPGGE  TPDGLDKEAS  EDSNIGALPN  QVSDLENQVS  ELDREVTRLP
SDLKDTEGNN  VGDYVKGGLE  KALTDEKVGL  NNTPKALDTA  PKALDTALNE  LGPDGDEEE

FIG. 7

Clade 6

BG6380  QALYESTQEQ  IEELKDYNEQ  ISEGEETLIL  AIQNKISDLD  DKIAEAKKL  ADSQNGEGVE
DYWTSGDEDK  LEKLQAEQDE  LQAELDQLLD  EVDGQE

FIG. 8

STRAIN SELECTION OF PNEUMOCOCCAL SURFACE PROTEINS

RELATED APPLICATIONS

This application is a continuation-in-part of application Ser. No. 08/465,746, filed Jun. 6, 1995, now U.S. Pat. No. 5,679,768, which is a continuation of application Ser. No. 08/048,896, filed Apr. 20, 1993, now abandoned.

Reference is made to U.S. application Ser. No. 08/714,741, filed Sep. 16, 1996, which is a continuation-in-part ("CIP") of U.S. Ser. No. 08/529,055, filed Sep. 15, 1995, which is a continuation-in-part of: application Ser. No. 08/226,844, filed May 29, 1992; application Ser. No. 08/093,907, filed Jul. 5, 1994; application Ser. No. 07/889,918, filed Jul. 5, 1994 (corresponding to PCT/US93/05191); application Ser. No. 08/482,981, filed Jun. 7, 1995; application Ser. No. 08/458,399, filed Jun. 2, 1995; application Ser. No. 08/446,201, filed May 19, 1995 (as a CIP of U.S. Ser. No. 08/246,636); application Ser. No. 08/246,636, filed May 20, 1994 (as a CIP U.S. Ser. No. 08/048,896, filed Apr. 20, 1993 as a CIP of U.S. Ser. No. 07/835,698, filed Feb. 12, 1992 as a CIP of U.S. Ser. No. 07/656,773); application Ser. No. 08/319,795, filed Oct. 7, 1994 (as a CIP of U.S. Ser. No. 08/246,636); application Ser. No. 08/072,070, filed Jun. 3, 1993; application Ser. No. 07/656,773, filed Feb. 15, 1991 (U.S. Ser. No. 656,773 and 835,698 corresponding to Int'l application WO 92/1448); application Ser. No. 08/246,636, filed May 20, 1994 (as a CIP of U.S. Ser. No. 08/048,896); and, each of these applications, as well as each document or reference cited in these applications, is hereby incorporated herein by reference. Documents or references are also cited in the following text, either in a Reference List before the claims, or in the text itself; and, each of these documents or references is hereby expressly incorporated herein by reference.

FIELD OF THE INVENTION

This invention relates to strain selection of PspAs from strains for vaccine compositions, based upon sequence homology and cross-reactivity. PspA strains can be classified according to sequence homology in the C-terminal region of the alpha helical region, and assigned to a clade, and subsequently, each clade is assigned to a family. Vaccine compositions of the present invention can comprise, at a minimum 2, and no more than 10 PspAs from strains from each clade, in order to develop a broadly efficacious pneumococcal vaccine with a limited number of strains.

BACKGROUND OF THE INVENTION

*Streptococcus pneumoniae* is an important cause of otitis media, meningitis, bacteremia and pneumonia, and a leading cause of fatal infections in the elderly and persons with underlying medical conditions, such as pulmonary disease, liver disease, alcoholism, sickle cell, cerebrospinal fluid leaks, acquired immune deficiency syndrome (AIDS), and patients undergoing immunosuppressive therapy. It is also a leading cause of morbidity in young children. Pneumococcal infections cause approximately 40,000 deaths in the U.S. yearly. The most severe pneumococcal infections involve invasive meningitis and bacteremia infections, of which there are 3,000 and 50,000 cases annually, respectively.

Despite the use of antibiotics and vaccines, the prevalence of pneumococcal infections has declined little over the last twenty-five years; the case-fatality rate for bacteremia is reported to be 15–20% in the general population, 30–40% in the elderly, and 36% in inner-city African Americans. Less severe forms of pneumococcal disease are pneumonia, of which there are 500,000 cases annually in the U.S., and otitis media in children, of which there are an estimated 7,000,000 cases annually in the U.S. caused by pneumococcus. Strains of drug-resistant *S. pneumoniae* are becoming ever more common in the U.S. and worldwide. In some areas, as many as 30% of pneumococcal isolates are resistant to penicillin. The increase in antimicrobial resistant pneumococcus further emphasizes the need for preventing pneumococcal infections.

Pneumococcus asymptomatically colonizes the upper respiratory tract of normal individuals; disease often results from the spread of organisms from the nasopharynx to other tissues during opportunistic events. The incidence of carriage in humans varies with age and circumstances. Carrier rates in children are typically higher than those of adults. Studies have demonstrated that 38 to 60% of preschool children, 29 to 35% of grammar school children and 9 to 25% of junior high school children are carriers of pneumococcus. Among adults, the rate of carriage drops to 6% for those without children at home, and to 18 to 29% for those with children at home. It is not surprising that the higher rate of carriage in children than in adults parallels the incidence of pneumococcal disease in these populations.

An attractive goal for streptococcal vaccination is to reduce carriage in the vaccinated populations and subsequently reduce the incidence of pneumococcal disease. There is speculation that a reduction in pneumococcal carriage rates by vaccination could reduce the incidence of the disease in non-vaccinated individuals as well as vaccinated individuals. This "herd immunity" induced by vaccination against upper respiratory bacterial pathogens has been observed using the *Haemophilus influenzae* type b conjugate vaccines (Takala, A. K., et al., J. Infect. Dis. 1991; 164: 982–986; Takala, A. K., et al., Pediatr. Infect. Dis. J., 1993; 12: 593–599; Ward, J., et al., *Vaccines*, S. A. Plotkin and E. A. Mortimer, eds., 1994, pp. 337–386; Murphy, T. V., et al., J. Pediatr., 1993; 122; 517–523; and Mohle-Boetani, J. C., et al., Pediatr. Infect. Dis. J., 1993; 12: 589–593).

It is generally accepted that immunity to *Streptococcus pneumoniae* can be mediated by specific antibodies against the polysaccharide capsule of the pneumococcus. However, neonates and young children fail to make adequate immune response against most capsular polysaccharide antigens and can have repeated infections involving the same capsular serotype. One approach to immunizing infants against a number of encapsulated bacteria is to conjugate the capsular polysaccharide antigens to protein to make them immunogenic. This approach has been successful, for example, with *Haemophilus influenzae* b (see U.S. Pat. No. 4,496,538 to Gordon and U.S. Pat. No. 4,673,574 to Anderson).

However, there are over ninety known capsular serotypes of *S. pneumoniae*, of which twenty-three account for about 95% of the disease. For a pneumococcal polysaccharide-protein conjugate to be successful, the capsular types responsible for most pneumococcal infections would have to be made adequately immunogenic. This approach may be difficult, because the twenty-three polysaccharides included in the presently-available vaccine are not all adequately immunogenic, even in adults.

Protection mediated by anti-capsular polysaccharide antibody responses are restricted to the polysaccharide type. Different polysaccharide types differentially facilitate virulence in humans and other species. Pneumococcal vaccines have been developed by combining 23 different capsular polysaccharides that are the prevalent types of human pneumococcal disease. These 23 polysaccharide types have been used in a licensed pneumococcal vaccine since 1983 (D. S. Fedson and D. M. Musher, Vaccines, S. A. Plotkin and J. E. A. Montimer, eds., 1994, pp. 517–564). The licensed 23-valent polysaccharide vaccine has a reported efficacy of approximately 60% in preventing bacteremia by type pneumococci in healthy adults.

However, the efficacy of the vaccine has been controversial, and at times, the justification for the recommended use of the vaccine questioned. It has been speculated that the efficacy of this vaccine is negatively affected by having to combine 23 different antigens. Having a large number of antigens combined in a single formulation may negatively affect the antibody responses to individual types within this mixture because of antigenic competition. The efficacy is also affected by the fact that the 23 serotypes encompass all serological types associated with human infections and carriage.

An alternative approach for protecting children, and also the elderly, from pneumococcal infection would be to identify protein antigens that could elicit protective immune responses. Such proteins may serve as a vaccine by themselves, may be used in conjunction with successful polysaccharide-protein conjugates, or as carriers for polysaccharides.

McDaniel et al. (I), J. Exp. Med. 160:386–397, 1984, relates to the production of hybridoma antibodies that recognize cell surface polypeptide(s) on S. pneumoniae and protection of mice from infection with certain strains of encapsulated pneumococci by such antibodies.

This surface protein antigen has been termed "pneumococcal surface protein A", or "PspA" for short.

McDaniel et al. (II), Microbial Pathogenesis 1:519–531, 1986, relates to studies on the characterization of the PspA. Considerable diversity in the PspA molecule in different strains was found, as were differences in the epitopes recognized by different antibodies.

McDaniel et al. (III), J. Exp. Med. 165:381–394, 1987, relates to immunization of X-linked immunodeficient (XID) mice with non-encapsulated pneutnococci expressing PspA, but not isogenic pneumococci lacking PspA, protects mice from subsequent fatal infection with pneumococci.

McDaniel et al. (IV), Infect. Immun., 59:222–228, 1991, relates to immunization of mice with a recombinant full length fragment of PspA that is able to elicit protection against pneumococcal strains of capsular types 6A and 3.

Crain et al, Infect.Immun., 56:3293–3299, 1990, relates to a rabbit antiserum that detects PspA in 100% (n=95) of clinical and laboratory isolates of strains of S. pneumoniae. When reacted with seven monoclonal antibodies to PspA, fifty-seven S. pneumoniae isolates exhibited thirty-one different patterns of reactivity.

Above cited applications 08/529,055, filed Sep. 15, 1995, 08/470,626, filed Jun. 6, 1995, 08/467,852, filed Jun. 6, 1995, 08/469,434, filed Jun. 6, 1995, 08/468,718, filed Jun. 6, 1995, 08/247,491, filed May 23, 1994, 08/214,222, filed Mar. 17, 1994 and 08/214,164, filed Mar. 17, 1994, 08/246, 636, filed May 20, 1994, and 08/319,795, filed Oct. 7, 1994, and U.S. Pat. No. 5,476,929, relate to vaccines comprising PspA and fragments thereof, methods for expressing DNA encoding PspA and fragments thereof, DNA encoding PspA and fragments thereof, the amino acid sequences of PspA and fragments thereof, compositions containing PspA and fragments thereof and methods of using such compositions.

PspA has been identified as a virulence factor and protective antigen. PspA is a cell surface molecule that is found on all clinical isolates, and the expression of PspA is required for the full virulence of pneumococci in mouse models (McDaniel et al., (III), J. Esp. Med. 165: 381–394, 1987). The biological function of PspA has not been well defined, although a preliminary report suggests that it may inhibit complement activation (Alonso DeVelasco, E., et al., Microbiological Rev. 1995; 59: 591–603).

The PspA protein type is independent of capsular type. It would seem that genetic mutation or exchange in the environment has allowed for the development of a large pool of strains which are highly diverse with respect to capsule, PspA, and possibly other molecules with variable structures. Variability of PspA's from different strains also is evident in their molecular weights, which range from 67 to 99 kD. The observed differences are stably inherited and are not the result of protein degradation.

Immunization with PspA in a lysate of a recombinant $\lambda$gt11 clone, elicited protection against challenge with several S. pneumoniae strains representing different capsular and PspA types, as in McDaniel et al. (IV), Infect. Immun. 59:222–228, 1991. Although clones expressing PspA were constructed according to that paper, the product was insoluble and isolation from cell fragments following lysis was not possible.

Analysis of the nucleotide and amino acid sequences indicate that the PspA molecule comprises three major regions. The first 288 amino acids at the amino terminal end of the protein are predicted to have a strong alpha helical structure. The adjacent region of 90 amino acids (289 to 369 of Rx1 PspA) has a high density of proline residues; based on similar regions in other prokaryotic proteins, this region is believed to transverse the bacterial cell wall. The remaining 196 amino acids at the carboxyl-terminal end of the molecule (370 to 588 of Rx1 PspA) have a repeated amino acid sequence that has been demonstrated to bind to phosphocholine and lipoteichoic acids. Based on this structure, the PspA molecule is thought to associate with the inner membrane and lipoteichoic acids via the repeated region in the middle of the carboxyl-terminal end of the protein. The proline region in the middle of the protein is thought to transverse the cell wall placing the alpha helical region on the outer surface of the S. pneumoniae cells. This model is consistent with the demonstration that the alpha helical region, which extends from the surface of the cell, contains the protective epitopes (Yother, J. et al., J. Bacteriol. 1992; 174: 601–609; Yother, J. et al., J. Bacteriol. 1994; 176: 2976–2985; McDaniel, L. S. et al., Microbial Pathog. 1994;

17: 323–337; and Ralph, B. A., et al., Ann. N.Y. Acad. Sci. 1994; 730: 361–363).

Serological analysis of PspA using a panel of seven monoclonal antibodies, indicated that, like capsular polysaccharides, the PspA molecules are highly diverse among pneumococcal strains. Based on these analyses, over 30 PspA protein serotypes were defined, and assignments of individual strains into group using a classification system, i.e., families (or serotypes), were based upon reactivity with the panel of monoclonal antibodies. Moreover, SDS-PAGE analysis indicated that within a PspA serotype, further heterogeneity existed on the basis of the molecular size. This diversification further supports the assertion that PspA is a protective antigen in natural infections; the protective nature of anti-PspA responses has presumably applied selective pressure on pneumococcus to diversify this molecule. However, this diversification of the PspA molecule complicates the development of a PspA vaccine, and leads to the possibility that a PspA vaccine would have to contain many PspA strains, possibly making the vaccine impractical.

In addition to the published literature specifically referred to above, the inventors, in conjunction with co-workers, have published further details concerning PspA's, as follows:

1. Abstracts of 89th Annual Meeting of the American Society for Microbiology, p. 125, item D-257, May 1989;
2. Abstracts of 90th Annual Meeting of the American Society for Microbiology, p. 98, item D-106, May 1990;
3. Abstracts of 3rd International ASM Conference on Streptococcal Genetics, p. 11, item 12, June 1990;
4. Talkington et al, Infect. Immun. 59:1285–1289, 1991;
5. Yother et al (I), J. Bacteriol. 174:601–609, 1992; and
6. Yother et al (II), J. Bacteriol. 174:610–618, 1992. 7. McDaniel et al (V), Microbiol. Pathogenesis, 13:261–268, 1994.

Alternative vaccination strategies are desirable as such provide alternative routes to administration or alternative routes to responses. It would be advantageous to provide an immunological composition or vaccination regimen which elicits protection against various diversified pneumococcal strains, without having to combine a large number of possibly competitive antigens within the same formulation.

OBJECTS AND SUMMARY OF THE INVENTION

It is an object of the present invention to provide a vaccine composition comprising at least two PspAs from strains selected from at least two families, a family being defined by PspAs from strains having greater than or equal to 50% homology in aligned sequences of a C-terminal region of an alpha helix of PspA.

Further, it is an object of the invention to provide vaccine compositions, wherein the families further comprise one or more clades, wherein clades are defined by one or more PspAs from strains, a PspA from a strain belonging to the clade having at least 75% homology with another PspA from a strain within the clade in the aligned sequences of the C-terminal region of the alpha helix of PspA.

Additionally, the present invention provides vaccine compositions wherein the C-terminal region comprises an epitope(s) of interest.

The present invention further provides vaccine compositions wherein a central domain comprising the C-terminal 100 amino acids of the alpha-helical region (192 to 290 of Rx1 PspA) is an epitope(s) capable of eliciting a protective immune response.

BRIEF DESCRIPTION OF THE FIGURES

Figure 3:
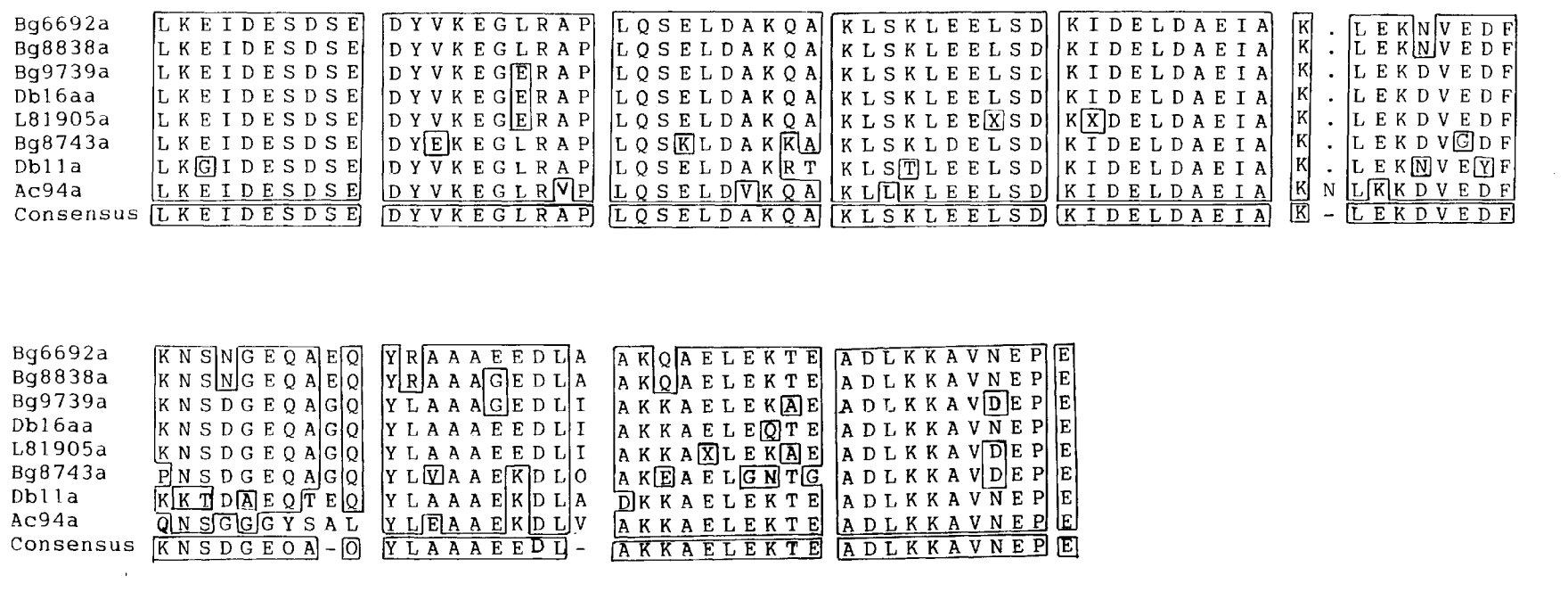

FIG. 3 shows the sequence identities of PspA clade 1 consensus, and corresponds to the data presented in Table 3;

Figure 4:
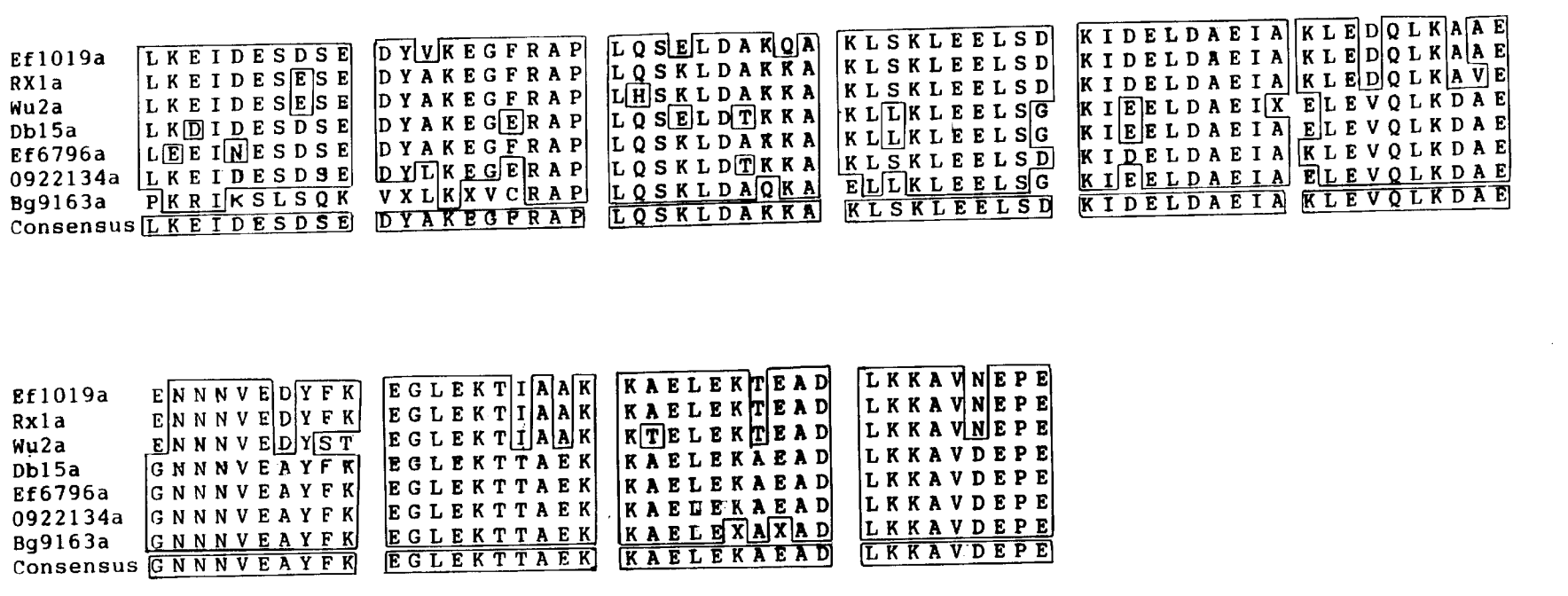

FIG. 4 shows the sequence identities to PspA clade 2 consensus, and corresponds to the data presented in Table 4;

FIG. 5 shows the sequence identities to PspA clade 3 consensus, and corresponds to the data presented in Table 5;

FIG. 6 shows the sequence identities to PspA clade 4 consensus, and corresponds to the data presented in Table 6;

FIG. 7 shows the sequence of PspA from strain ATCC6303, a representative strain of clade 5;

FIG. 8 shows the sequence of PspA from strain BG6380 (ATCC 55838, American Type Culture Collection, 12301 Parklawn Drive, Rockville, Md. 20852) a representative strain of clade 6;

DETAILED DESCRIPTION

Figure 1:
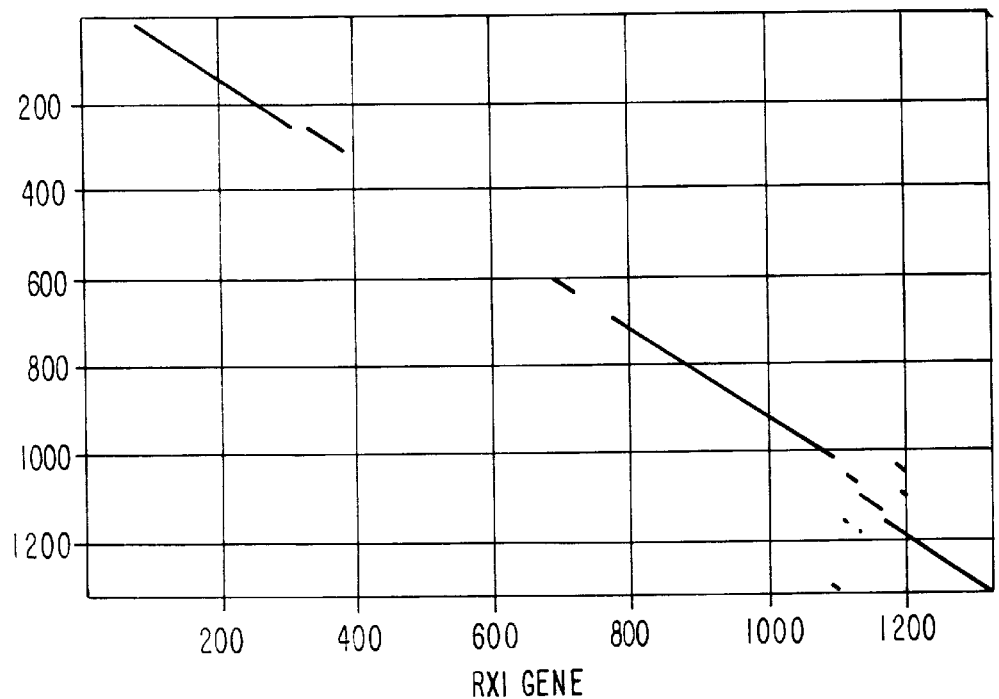
FIG. 1 shows a Pustell DNA matrix analysis of homology between the PspA genes of Rx1 (ATCC 55334, American Type Culture Collection, 12301 Parklawn Drive, Rockville, Md. 20852) and EF10197 strains.
Figure 2:
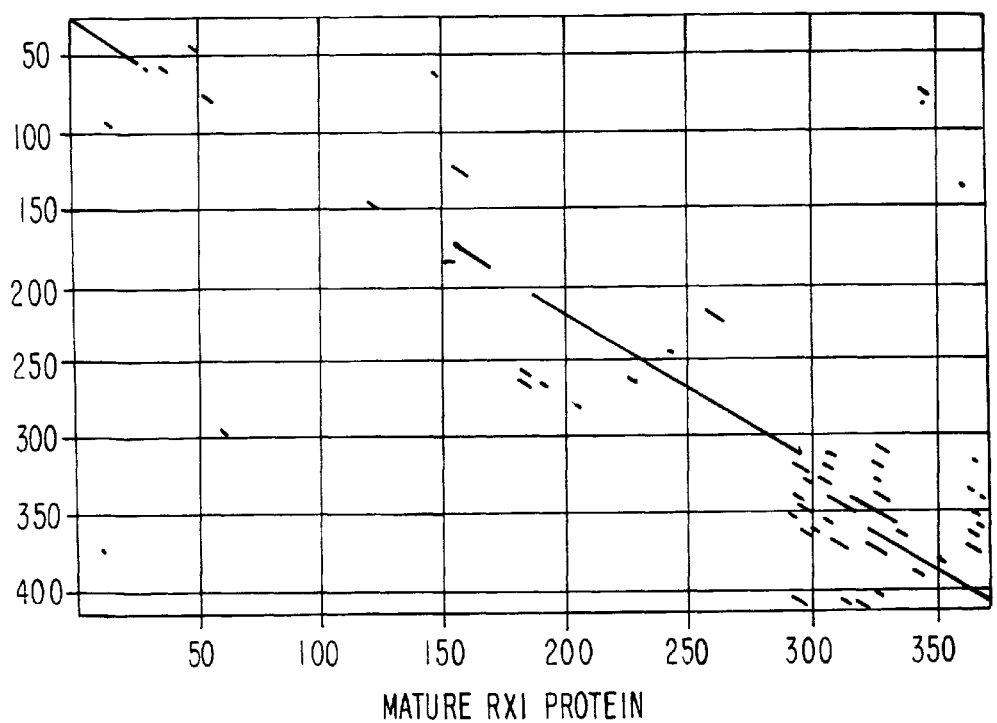
FIG. 2 shows a Pustell protein matrix analysis of homology between the PspA proteins of Rx1 (ATCC 55834) and EF10197 strains.

It has now been surprisingly found that, despite the assertions of the prior art regarding the apparent diversity of PspA from strains, the primary sequence of the alpha helix of PspA has two regions of relative conservation and a region of extensive diversity between PspAs from strains. The two regions of relative conservation are comprised of the first, N-terminal, 60 amino acids of the alpha helix, and the last, C-terminal, about 100 amino acids of the alpha helix, as shown in FIGS. 1 and 2, wherein the C-terminal end of the alpha helix contains cross-reactive and protective epitopes that are critical to the development of a broadly efficacious PspA vaccine. It has been found that any conservation in the first, N-terminal, 60 amino acids of the alpha helix is of little consequence in the cross-reactivity of the strain, and hence, is irrelevant to the development of a PspA vaccine.

A comparison of the amino acid sequences in the C-terminal region of the alpha helix of PspAs from 24 strains of S. pneumoniae, has revealed that the PspA strains can be grouped into 6 clades with greater than 75% homology, and these clades could be grouped into 4 families with greater than 50% homology.

Accordingly, the present invention provides a method of strain selection of PspA, based upon the sequence homology of PspAs in the C-terminal region of the alpha helix.

A clade is defined herein as comprising PspAs which exhibit greater than 75% sequence homology in aligned sequences of the C-terminal region of the alpha helix, and a family is defined herein as those clades which exhibit greater than or equal to 50% homology between member PspA sequences in aligned sequences of the C-terminal region of the alpha helix.

Further, it has been found that in addition to sequence homology, members of a clade exhibit cross-reactivity and cross-protection among one another, which may suggest a causal relationship between sequence homology and cross-reactivity. PspAs of strains within the same PspA clade exhibit reciprocal cross-protection from immunization and challenge experiments. It has not been heretofore recognized in the prior art that there may be such a causal relationship; in fact, families of PspA strains were defined solely on the basis of serological cross-reactivity, and based upon the prior art definition of families of PspA strains, it was believed that the extreme diversity of the PspA molecule would result in a futile attempt at strain selection. Moreover, the PspA typing system (Crain, et al., Infect. Immun. 59: 222–228, 1990) failed to provide relevant groupings of strains, and suggested an enormous diversity.

Hence, the present invention, in contrast to the teachings of the prior art, enables the selection of PspAs from strains in accordance with sequence homology and cross-reactivity, which facilitates the development of vaccine compositions comprising multiple PspAs.

The present invention contemplates vaccine compositions comprising two or more, preferably no more than 10, and more preferably a minimum of 4 and a maximum of 6 strains of PspA representing a single clade each, and a pharmaceutically acceptable carrier or diluent. In a preferred embodiment, Rx1, (ATCC 55834) a member of clade 2, is the preferred strain of clade 2 and/or family 1 which is optionally included in the vaccine composition of the present invention.

The aforementioned definition of a family structure to the C-terminal end of the alpha helix region enables the development of a broadly efficacious pneumococcal vaccine composition with a limited number of strains. Combining strains that represent some or all of the families for this cross-reactive and protective region should provide broad protection against pneumococcal disease. Not all clades may need to be represented because of cross-reactions between some clades within families or because of the epidemiology of these strains or clades in the population to be vaccinated. However, it is well within the scope of knowledge of the skilled artisan to determine those strains which should be included within a vaccine composition, without the burden of undue experimentation.

Additionally, the selected PspAs of the present invention further comprise an epitope(s) of interest which can elicit a immune response. An epitope of interest is an antigen or immunogen or immunologically active fragment thereof from a pathogen or toxin of veterinary or human interest.

The present invention provides an immunogenic, immunological or vaccine composition containing pneumococcal strain(s) having an epitope of interest, and a pharmaceutically acceptable carrier or diluent. An immunological composition containing the PspAs having an epitope of interest, elicits an immunological response—local or systemic. The response can, but need not be, protective. An immunogenic composition containing the PspAs having an epitope of interest, likewise elicits a local or systemic immunological response which can, but need not be, protective. A vaccine composition elicits a local or systemic protective response. Accordingly, the terms "immunological composition" and "immunogenic composition" include a "vaccine composition" (as the two former terms can be protective compositions).

The invention therefore also provides a method of inducing an immunological response in a host mammal comprising administering to the host an immunogenic, immunological or vaccine composition comprising PspAs having an epitope of interest, and a pharmaceutically acceptable carrier or diluent.

As to epitopes of interest, one skilled in the art can determine an epitope of immunodominant region of a peptide or polypeptide, and ergo, the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

A general method for determining which portions of a protein to use in an immunological composition focuses on the size and sequence of the antigen of interest. "In general, large proteins, because they have more potential determinants are better antigens than small ones. The more foreign an antigen, that is the less similar to self configurations which induce tolerance, the more effective it is in provoking an immune response." Ivan Roitt, *Essential Immunology,* 1988.

At a minimum, the peptide can be at least 8 or 9 amino acids long. This is the minimum length that a peptide needs to be in order to stimulate a CD4+T cell response which recognizes virus infected cells or cancerous cells). A minimum peptide length of 13 to 25 amino acids is useful to stimulate a CD8+T cell response (which recognizes special antigen presenting cells which have engulfed the pathogen). See Kendrew, supra. However, as these are minimum lengths, these peptides are likely to generate an immunological response, i.e., an antibody or T cell response; but, for a protective response (as from a vaccine composition), a longer peptide is preferred.

With respect to the sequence, the DNA sequence encoding the immunogenic peptide preferably encodes at least regions of the peptide that generate an antibody response or a T cell response. One method to determine T and B cell epitopes involves epitope mapping. The protein of interest "is fragmented into overlapping peptides with proteolytic enzymes. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules. The method is less effective for determining B-cell epitopes" since B cell epitopes are often not linear amino acid sequence but rather result from the tertiary structure of the folded three dimensional protein. Janis Kuby, *Immunology*, (1992) pp. 79–80.

In the case of PspA, the location of the major cross-reactive region at the C-terminal 100 amino acids of the alpha-helical region was carried out with recombinant peptides of 100 or more amino acids in length (McDaniel et al., Micro. Pathog. 17: 323–337, 1994).

Another method for determining an epitope of interest is to choose the regions of the protein that are hydrophilic. Hydrophilic residues are often on the surface of the protein and therefore often the regions of the protein which are accessible to the antibody. Janis Kuby, *Immunology*, (1992) P. 81.

Yet another method for determining an epitope of interest is to perform an X-ray cyrstallographic analysis of the antigen (full length)-antibody complex. Janis Kuby, *Immunology*, (1992) p. 80.

Still another method for choosing an epitope of interest which can generate a T cell response is to identify from the protein sequence potential HLA anchor binding motifs which are peptide sequences which are known to be likely to bind to the MHC molecule.

The peptide which is a putative epitope, to generate a T cell response, should be presented in a MHC complex. The peptide preferably contains appropriate anchor motifs for binding to the MHC molecules, and should bind with high enough affinity to generate an immune response. Factors which can be considered are: the HLA type of the patient (vertebrate, animal or human) expected to be immunized, the sequence of the protein, the presence of appropriate anchor motifs and the occurance of the peptide sequence in other vital cells.

An immune response is generated, in general, as follows: T cells recognize proteins only when the protein has been cleaved into smaller peptides and is presented in a complex called the "major histocompatability complex MHC" located on another cell's surface. There are two classes of MHC complexes—class I and class II, and each class is made up of many different alleles. Different patients have different types of MHC complex alleles; they are said to have a 'different HLA type'.

Class I MHC complexes are found on virtually every cell and present peptides from proteins produced inside the cell. Thus, Class I MHC complexes are useful for killing cells which when infected by viruses or which have become cancerous and as the result of expression of an oncogene. T cells which have a protein called CD4 on their surface, bind to the MHC class I cells and secrete lymphokines. The lymphokines stimulate a response; cells arrive and kill the viral infected cell.

Class II MHC complexes are found only on antigen-presenting cells and are used to present peptides from circulating pathogens which have been endocytosed by the antigen-presenting cells. T cells which have a protein called CD8 bind to the MHC class II cells and kill the cell by exocytosis of lytic granules.

Some guidelines in determining whether a protein is an epitope of interest which will stimulate a T cell response, include: Peptide length—the peptide should be at least 8 or 9 amino acids long to fit into the MHC class I complex and at least 13–25 amino acids long to fit into a class II MHC complex. This length is a minimum for the peptide to bind to the MHC complex. It is preferred for the peptides to be longer than these lengths because cells may cut the expressed peptides. The peptide should contain an appropriate anchor motif which will enable it to bind to the various class I or class II molecules with high enough specificity to generate an immune response (See Bocchia, M. et al, *Specific Binding of Leukemia Oncogene Fusion Protein Peptides to HLA Class I Molecules*, Blood 85:2680–2684; Englehard, V H, *Structure of peptides associated with class I and class II MHC molecules* Ann. Rev. Immunol. 12:181 (1994)). This can be done, without undue experimentation, by comparing the sequence of the protein of interest with published structures of peptides associated with the MHC molecules. Protein epitopes recognized by T cell receptors are peptides generated by enzymatic degradation of the protein molecule and are presented on the cell surface in association with class I or class II MHC molecules.

Further, the skilled artisan can ascertain an epitope of interest by comparing the protein sequence with sequences listed in the protein data base. Regions of the protein which share little or no homology are better choices for being an epitope of that protein and are therefore useful in a vaccine or immunological composition. Regions which share great homology with widely found sequences present in vital cells should be avoided.

Even further, another method is simply to generate or express portions of a protein of interest, generate monoclonal antibodies to those portions of the protein of interest, and then ascertain whether those antibodies inhibit growth in vitro of the pathogen from which the protein was derived. The skilled artisan can use the other guidelines set forth in this disclosure and in the art for generating or expressing portions of a protein of interest for analysis as to whether antibodies thereto inhibit growth in vitro. For example, the skilled artisan can generate portions of a protein of interest by: selecting 8 to 9 or 13 to 25 amino acid length portions of the protein, selecting hydrophylic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response one skilled in the art can preferably perform an epitope map, using the general methods described above, or other mapping methods known in the art.

As can be seen from the foregoing, without undue experimentation, from this disclosure and the knowledge in the art, the skilled artisan can ascertain the amino acid and corresponding DNA sequence of an epitope of interest for obtaining a T cell, B cell and/or antibody response. In addition, reference is made to Gefter et al., U.S. Pat. No. 5,019,384, issued May 28, 1991, and the documents it cites, incorporated herein by reference (Note especially the "Relevant Literature" section of this patent, and column 13 of this patent which discloses that: "A large number of epitopes have been defined for a wide variety of organisms of interest. Of particular interest are those epitopes to which neutralizing antibodies are directed. Disclosures of such epitopes are in many of the references cited in the Relevant Literature section.")

Further, the invention demonstrates that more than one serologically complementary PspA molecule can be in an antigenic, immunological or vaccine composition, so as to elicit better response, e.g., protection, for instance, against a variety of strains of pneumococci; and, the invention provides a system of selecting PspAs for a multivalent composition which includes cross-protection evaluation so as to provide a maximally efficacious composition.

The determination of the amount of antigen, e.g., PspA or truncated portion thereof and optional adjuvant in the inventive compositions and the preparation of those compositions can be in accordance with standard techniques well known to those skilled in the pharmaceutical or veterinary arts. In particular, the amount of antigen and adjuvant in the inventive compositions and the dosages administered are determined by techniques well known to those skilled in the medical or veterinary arts taking into consideration such factors as the particular antigen, the adjuvant (if present), the age, sex, weight, species and condition of the particular patient, and the route of administration. For instance, dosages of particular PspA antigens for suitable hosts in which an immunological response is desired, can be readily ascertained by those skilled in the art from this disclosure, as is the amount of any adjuvant typically administered therewith. Thus, the skilled artisan can readily determine the amount of antigen and optional adjuvant in compositions and to be administered in methods of the invention. Typically, an adjuvant is commonly used as 0.001 to 50 wt % solution in phosphate buffered saline, and the antigen is present on the order of micrograms to milligrams, such as about 0.0001 to about 5 wt %, preferably about 0.0001 to about 1 wt %, most preferably about 0.0001 to about 0.05 wt % (see, e.g., Examples below or in applications cited herein).

Typically, however, the antigen is present in an amount on the order of micrograms to milligrams, or, about 0.001 to about 20 wt %, preferably about 0.01 to about 10 wt %, and most preferably about 0.05 to about 5 wt %.

Of course, for any composition to be administered to an animal or human, including the components thereof, and for any particular method of administration, it is preferred to determine therefor: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable immunological response, such as by titrations of sera and analysis thereof for antibodies or antigens, e.g., by ELISA and/or RFFIT analysis. Such determinations do not require undue experimentation from the knowledge of the skilled artisan, this disclosure and the documents cited herein. And, the time for sequential administrations can be ascertained without undue experimentation.

Examples of compositions of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention, are conveniently provided as liquid preparations, e.g., isotonic aqueous solutions, suspensions, emulsions or viscous compositions which may be buffered to a selected pH. If digestive tract absorption is preferred, compositions of the invention can be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or, a dose having a particular particle size.

Compositions of the invention can contain pharmaceutically acceptable flavors and/or colors for rendering them more appealing, especially if they are administered orally. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally, to animals, children, particularly small children, and others who may have difficulty swallowing a pill, tablet, capsule or the like, or in multi-dose situations. Viscous compositions, on the other hand, can be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the antigen, lipoprotein and optional adjuvant. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to the PspA antigen and optional adjuvant. This will present no problem to those skilled in chemical and pharmaceutical principles, or problems can be readily avoided by reference to standard texts or by simple experiments (not involving undue experimentation), from this disclosure and the documents cited herein.

The immunologically effective compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Gererally the pH may be from about 3 to 7.5. Compositions can be administered in dosages and by techniques well known to those skilled in the medical and veterinary arts taking into consideration such factors as the age, sex, weight, and condition of the particular patient or animal, and the composition form used for administration (e.g., solid vs. liquid). Dosages for humans or other mammals can be determined without undue experimentation by the skilled artisan, from this disclosure, the documents cited herein, the Examples below (e.g., from the Examples involving mice).

Suitable regimes for initial administration and booster doses or for sequential administrations also are variable, may include an initial administration followed by subsequent administrations; but nonetheless, may be ascertained by the skilled artisan, from this disclosure, the documents cited herein, and the Examples below.

The following Examples are provided for illustration and are not to be considered a limitation of the invention.

EXAMPLES

Example 1

Identification of Sequence Homologies Between PspAs

Despite the described diversity of PspA strains, the nucleotide and amino acids sequences of the PspA molecule has been evaluated with respect to whether any region(s) of conservation have been maintained which could be of utility to vaccine development. The comparison of the nucleotide and amino acid sequences from multiple strains of PspA revealed that the primary sequence of the alpha helix has two regions of relative conservation, and a region of extensive diversity between strains. The two regions of diversity are comprised of the first, N-terminal, 60 amino acids of the alpha helix, and the last, C-terminal, 100 amino acids of the alpha helix, as shown in FIGS. 1 and 2.

FIG. 1 shows the nucleotide sequences of the alpha helix and proline regions of the pspA genes from Rx1 (ATCC 55834) and EF10197, both members of the same family or clade, as compared to each other for regions of homology. This comparison was made used a Pustell DNA matrix analysis within the MacVector version 5.0.2 software, using a window of 30 nucleotides, a minimum percentage of homology of 70%, a hash value of 6, and a jump value of 1. Points or lines in the graph indicate regions of homology between the two genes that meet the aforementioned criteria. The results demonstrate homology in the portions of the genes encoding the N-terminal and C-terminal ends of the alpha helix region, as well as the proline region.

FIG. 2 shows the amino acid sequence comparison of the alpha helix and proline regions of the PspA proteins from Rx1 and EF10197, both members of the same family or clade, as compared to each other for regions of homology. This comparison was made using a Pustell protein matrix analysis within the MacVector version 5.0.2 software. The analysis was done using a window of 8 amino acids, a minimum percentage homology of 70%, a hash value of 2, and the pam250 scoring matrix. Points or lines in the graph indicate regions of homology between the two proteins. The results demonstrate homology in the N-terminal and the C-terminal ends of the alpha helix region, as well as in the proline region.

The conserved region at the C-terminal end of the alpha helix region correlated with a region demonstrated to contain protective epitopes that were conserved between two strains.

Expecting that the C-terminal region of the alpha helix region was critical to vaccine development, the heterogeneity and family structure of amino acid sequences in this region was examined. The comparison of the amino acid sequences in this region between 26 strains of PspA revealed that the PspA strains could be grouped into 6 clades with greater than 75% homology. These clades could be grouped into 4 families with greater than 50% homology. This data is shown in Tables 1 to 6, and FIGS. 3 to 8.

TABLE 1

Family/Clade List

| FAMILY | HOMOLOGY WITHIN FAMILY | CLADE | STRAIN | % AMINO ACID HOMOLOGY TO CLADE CONSENSUS |
|---|---|---|---|---|
| Family 1 | >50% | Clade 1 | BG9739 | 96 |
| | | | DBL6A | 98 |
| | | | L81905 | 94 |
| | | | BG8743 | 87 |
| | | | AC94 | 88 |
| | | | BG6692 | 96 |
| | | | BG8838 | 95 |
| | | | DBL1 | 88 |
| | | Clade 2 | EF10197 | 89 |
| | | | RX1 | 92 |
| | | | WU2 | 87 |
| | | | 0922134 | 99 |
| | | | DBL5 | 92 |
| | | | BG9163 | 79 |
| | | | EF6796 | 91 |
| Family 2 | >50% | Clade 3 | EF3296 (ATCC 558535) | 97 |
| | | | AC122 | 96 |
| | | | BG8090 | 96 |
| Family 3 | >50% | Clade 4 | EF5668 (ATCC 55836) | 92 |
| | | | BG7817 | 96 |
| | | | BG7561 | 89 |
| | | | BG11703 | 100 |
| | | Clade 5 | ATCC6303 | 100 |
| Family 4 | >50% | Clade 6 | BG6380 (ATCC 55838) | 100 |

TABLE 2A

Homology Between Clades - Matrix of Amino Acid Similarity Estimates Between Clades

| | Clade 1 | Clade 2 | Clade 3 | Clade 4 | Clade 5 | Clade 6 |
|---|---|---|---|---|---|---|
| Clade 1 | >75% | | | | | |
| Clade 2 | >50% | >75% | | | | |
| Clade 3 | <25% | <20% | >75% | | | |
| Clade 4 | <20% | >30% | >30% | >75% | | |
| Clade 5 | <20% | <20% | >30% | >50% | >75% | |
| Clade 6 | <10% | <20% | <10% | <20% | <20% | >75% |

TABLE 2B

AA% sequence identities to PspA Clade Consensus

| Clade | Strain Name (Capsular Type) | % of AA that differ from the Clade Consensus | % AA identity to Clade Consensus |
|---|---|---|---|
| Clade 1 | BG9739 (ATCC 55837) (4) | 4 | 96 |
| | DBL6A (6A) | 2 | 98 |
| | L81905 (4) | 6 | 94 |
| | BG8743 (23) | 13 | 87 |

TABLE 2B-continued

AA% sequence identities to PspA Clade Consensus

| Clade | Strain Name (Capsular Type) | % of AA that differ from the Clade Consensus | % AA identity to Clade Consensus |
|---|---|---|---|
| | AC94 (9) | 12 | 88 |
| | BG6692 (33) | 4 | 96 |
| | BG8838 (6) | 5 | 95 |
| | DBL1 (6B) | 12 | 88 |
| Clade 2 | EF10197 (3) | 10 | 89 |
| | RX1 (2) | 8 | 92 |
| | WU2 (3) | 13 | 87 |
| | 0922134 (23) | 1 | 99 |
| | DBL5 (5) | 8 | 92 |
| | BG9163 (6B) | 21 | 79 |
| | EF6796 (6A) | 9 | 91 |
| Clade 3 | EF3296 (ATCC 55835) (4) | 1 | 97 |
| | AC122 (9) | 2 | 96 |
| | BG8090 (19) | 4 | 96 |
| Clade 4 | EF5668 (4) | 9 | 92 |
| | BG7817 (7) | 4 | 96 |
| | BG7561 (15) | 12 | 89 |
| | BG11703 (N.D) | 0 | 100 |
| Clade 5 | ATCC6303 (3) | 0 | 100 |
| Clade 6 | BG6380 (ATCC 55838) (37) | 0 | 100 |

N.D. = not determined

TABLE 3

Sequence identities to PspA Clade 1 Consensus

| CLADE | STRAIN NAME | # OF AA THAT DIFFER FROM THE CLADE CONSENSUS | % AA IDENTITY TO CLADE CONSENSUS |
|---|---|---|---|
| Clade 1 | BG9739 (ATCC 55837) | 4 | 96 |
| | DBL6A | 2 | 98 |
| | L81905 | 6 | 94 |
| | BG8743 | 13 | 87 |
| | AC94 | 12 | 88 |
| | BG6692 | 4 | 96 |
| | BG8838 | 5 | 95 |
| | DBL1 | 12 | 88 |

TABLE 4

Sequence identities to PspA Clade 2 consensus

| CLADE | STRAIN NAME | # OF AA THAT DIFFER FROM THE CLADE CONSENSUS | % AA IDENTITY TO CLADE CONSENSUS |
|---|---|---|---|
| Clade 2 | EF10197 | 10 | 89 |
| | RX1 (ATCC 55834) | 8 | 92 |
| | WU2 | 13 | 87 |
| | 0922134 | 1 | 99 |
| | DBL5 | 8 | 92 |
| | BG9163 | 21 | 79 |
| | EF6796 | 9 | 91 |
| | RCT123 | 3 | 97 |
| | RCT129 | 1 | 99 |
| | RCT135 | 0 | 100 |
| | LXS200 | 0 | 100 |

TABLE 5

Sequence identities to PspA Clade 3 Consensus

| CLADE | STRAIN NAME | # OF AA THAT DIFFER FROM THE CLADE CONSENSUS | % AA IDENTITY TO CLADE CONSENSUS |
|---|---|---|---|
| Clade 3 | EF3296 (ATCC 55835) | 1 | 97 |
| | AC122 | 2 | 96 |
| | BG8090 | 4 | 96 |

TABLE 6

Sequence identities to PspA Clade 4 Consensus

| CLADE | STRAIN NAME | # OF AA THAT DIFFER FROM THE CLADE CONSENSUS | % AA IDENTITY TO CLADE CONSENSUS |
|---|---|---|---|
| Clade 4 | EF5668 (ATCC 55836) | 9 | 92 |
| | BG7817 | 4 | 96 |
| | BG7561 | 12 | 89 |
| | BG11703 | 0 | 100 |

The immunological relevance of these families was demonstrated by serological analysis of *S. pneumoniae* strains with a large number of monoclonal antibodies made to several different PspAs. As shown in Table 7, the pattern of reactions with strains in clades 3, 4, 5 and 6 of monoclonal antibodies generally correlated with the defined clade by sequence.

Figure 9:
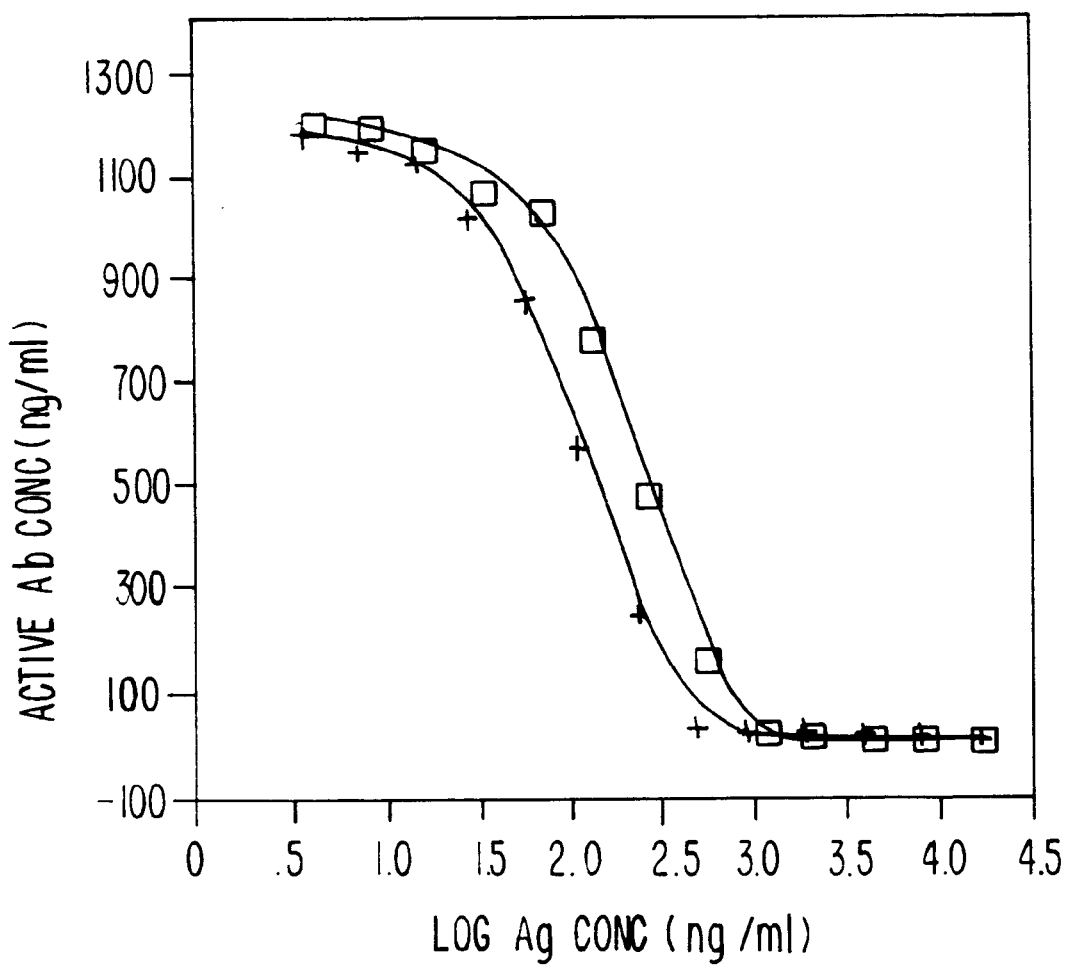
FIG. 9 shows the competitive inhibition of rabbit polyclonal anti-Rx1 by PA314, recombinant Rx1 (ATCC 55834) containing amino acids 96 to 314.

Competitive inhibition of anti-PARx1 binding to PARx1 antigen was analyzed using a BIAcore® sensory chip, coated with PARx1 antigen. The results are shown in FIG. 9. Rabbit polyclonal anti-PARx1 (1200 ng/ml) was allowed to react to the chip either alone, or in the presence of increasing concentration of PARx1 antigen (indicated by+in FIG. 9) or PA314 PspA antigen (indicated by squares in FIG. 9); the PA314 PspA antigen contains amino acids 96 to 314 of Rx1(ATCC 55834). The concentration of uninhibited antibody able to bind to the PARx1 antigen on the sensory chip surface was measured using mass transport measurements on the BIAcore® instrument. The mouse monoclonal IgG anti-PspA antibody, P81-122FI0.A11 was used as a standard for these measurements.

The results of these experiments indicated that the N-terminal conserved region does not contain antigenic epitopes for the PspA response, and that the conserved region at the C-terminal end of the alpha helix contains cross-reactive and protective epitopes that are critical to the development of a broadly efficacious PspA vaccine. Further, FIG. 9 demonstrates the lack of relevance of the first 60 amino acids of the N-terminal region of the alpha helix, as the PA314 PspA antigen used in the competition assays above, contains amino acids 96 to 314 of Rx1.

Figure 10:
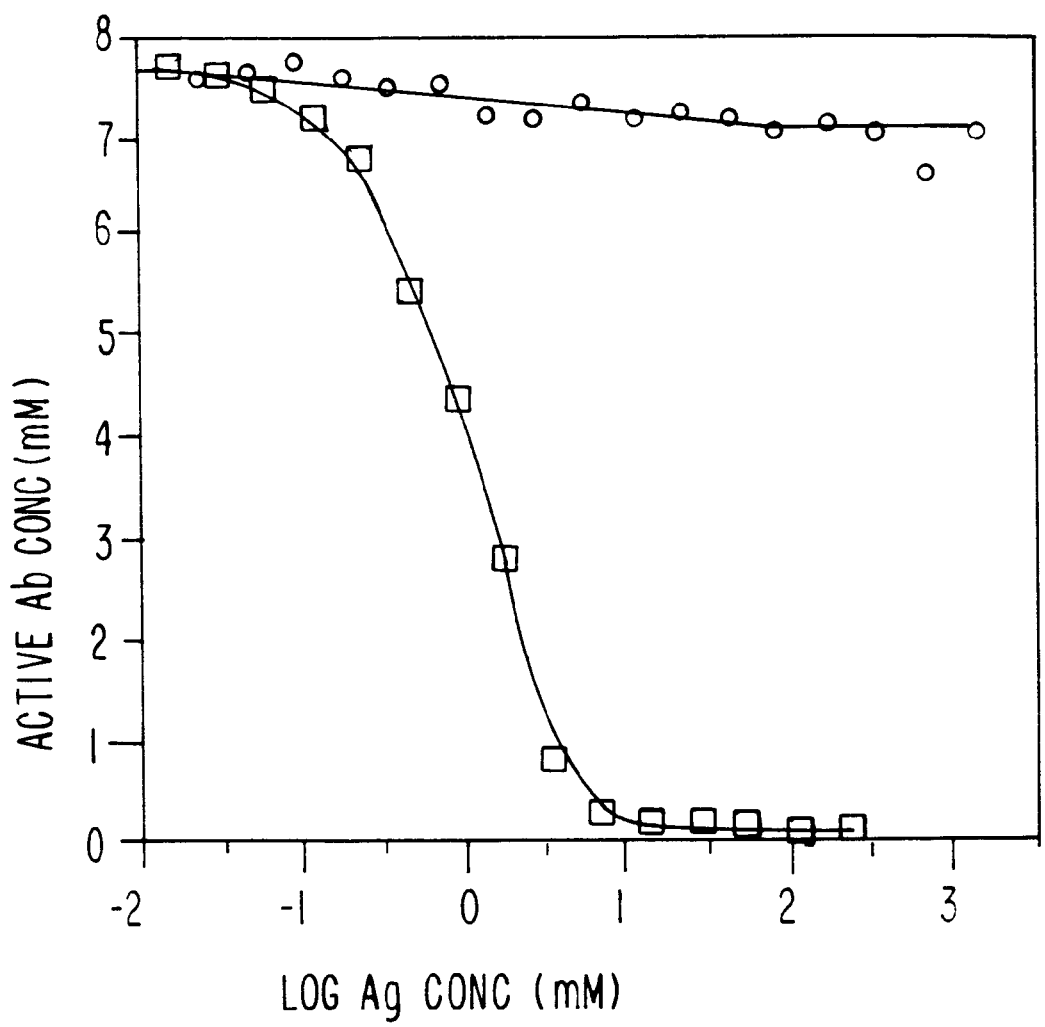
FIG. 10 shows the inhibition of polyclonal rabbit anti-Rx1 antibodies by PARx1 and PAEF5668 antigens.

FIG. 10 shows the inhibition of PARx1 and PAEF5668 antigens. A BIAcore® sensory chip was coated with PARx1 antigen and rabbit polyclonal anti-PARx1 (7 mM) was allowed to react to the chip either alone, or in the presence of increasing concentration of PARx1 antigen (represented by squares in FIG. 10) or PAEF5668 antigen (represented by diamonds in FIG. 10). The concentration (mM) of these competitive antigens is shown on the X axis on a logarithmic

TABLE 7

Ab Reactions Clades 3-6

| | | Anti-PspA Monoclonal Antibodies | | | | | | | | | |
|---|---|---|---|---|---|---|---|---|---|---|---|
| | | Made to EF3296 (P32) | | | | | | Made to EF5668 (P56) | | | |
| STRAIN | CLADE* | 263D12 | 263F6 | 264A4 | 264A11 | 265E6 | 270B6 | 263B7 | 351G12 | 350B4 | 348G7 | 350H12 |
| EF3296 (ATCC 55835) | 3 | X | X | X | X | X | X | X | | | | |
| BG7140 | | X | | X | X | X | X | | | | | |
| PMsv1281 | | X | X | X | X | | X | X | | | | |
| VH1193 | | X | X | X | X | X | X | X | | | | |
| EF5668 (ATTC 55836) | 4 | | | | | | | | X | X | X | X |
| BG7817 | 4 | | | | | | | | X | X | X | X |
| BG7561 | 4 | | | | | | | | X | X | X | X |
| BG11703 | 4 | | | | | | | | X | X | X | X |
| BG7736 | | | | | | | | | X | X | X | X |
| BG7813 | | | | | | | | | X | X | X | X |
| BG7915 | | | | | | | | | X | X | X | X |
| BG10717/30 | | | | | | | | | X | X | X | X |
| ATCC 6306 | 5 | | | | | | | | X | X | | |
| BG7619 | | | | | | | | | X | X | | |
| BG7941 | | | | | | | | | X | X | | |
| BG13075/30 | | | | | | | | | X | X | | |
| BG6380 | 6 | | | | | | | | | | | |

X indicates a positive reaction
*clade was determined by amino acid sequences

Example 2

Competitive Inhibition of Anti-Rx1 Polyclonal Antibodies with the PspA Antigens of Different Strains scale, while the concentration (mM) of uninhibited polyclonal antibody able to bind to the PARx1 antigen on the sensory chip was measured using mass transport measurements on the BIAcore® instrument, and is shown on the Y axis in FIG. 10.

As expected, the concentration of active, non-competitively inhibited polyclonal anti-PARx1 decreased as the concentrations of competitive inhibitor increased. PARx1 antigen completely inhibited the polyclonal antibodies at sufficient concentrations of antigens in excess. The PAEF5668 antigen has a maximal inhibition of 8.4%. The mouse monoclonal IgG anti-PspA antibody, P81-122F10.A11 was used as a standard for calculating the concentrations of active polyclonal antibody in this assay.

Figure 11:
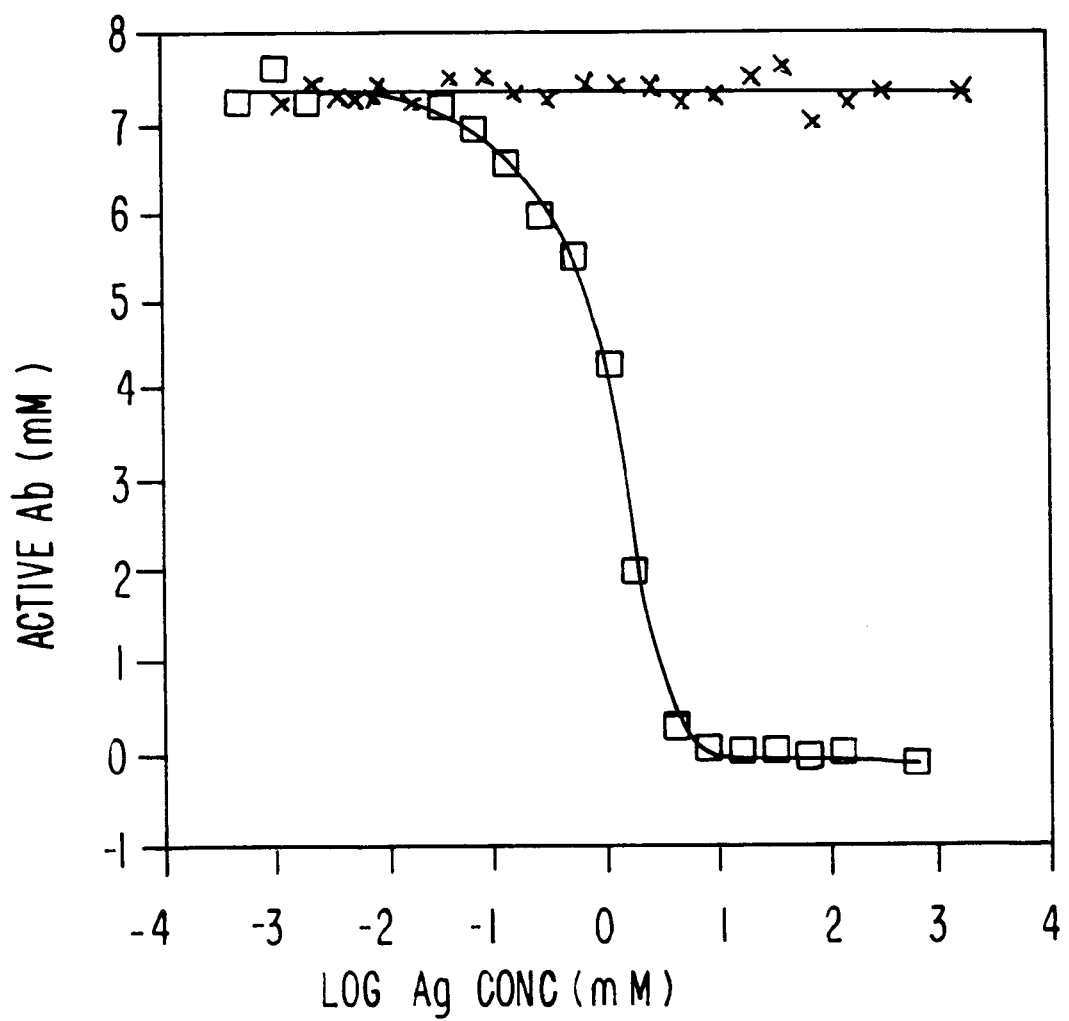
FIG. 11 shows the inhibition of polyclonal rabbit anti-Rx1 antibodies by PARx1 and PABG6380 antigens.

The results of the inhibition study by PARx1 and PABG6380 antigens is shown in FIG. 11. A BIAcore® sensory chip was coated with PARx1 antigen and rabbit polyclonal anti-PARx1 (7 mM) was allowed to react to the chip either alone, or in the presence of increasing concentration of PARx1 antigen (represented by squares in FIG. 11), or PABG6380 antigens (represented by X's in FIG. 11). The concentration (mM) of these competitive antigens is shown on the X axis on a logarithmic scale, while the concentration (mM) of uninhibited polyclonal antibody able to bind to the PARx1 antigen on the sensory chip was measured using mass transport measurements on the BIAcore® instrument, and is shown on the Y axis in FIG. 11.

As expected, the concentration of active, non-competitively inhibited polyclonal anti-PARx1 decreased as the concentration of competitive inhibitor increased. PARx1 antigen completely inhibited the polyclonal antibodies at sufficient concentrations of antigen in excess. The PABG6380 antigen did not significantly inhibit the polyclonal antibody reaction. The mouse monoclonal IgG anti-PspA antibody, P81-122F10.A11 was used as a standard for calculating the concentrations of active polyclonal antibody in the assay.

Further, Table 8 shows the results of inhibition studies of polyclonal rabbit anti-Rx1 antibodies with representative strains of selective clades. As shown in the Table, anti-Rx1 antibodies inhibit clade 2 effectively, but the inhibition of PspAs in clades which differ from the specificity of the antibody itself is less effective.

TABLE 8

Inhibition of Polyclonal Rabbit anti-Rx1 Antibodies (Inhibition of Anti-Clade 2 Antibody Reactivity

| Clade | 1 | 2 | 2 | 2 | 4 | 6 | — |
|---|---|---|---|---|---|---|---|
| Strain | BG9739 (ATCC 55837) | RX1 (ATCC 55834) | R36A | WU2 | EF5668 (ATCC 55836) | BG6380 (ATCC 55638) | JY1119* |
| Antigen Name | BG9739/n | PARx1 | R36A/n | WU2/n | PAEF5668 | PABG6380 | JY1119/n |
| Antigen Type | native | recom.** | native | native | recom.** | recom.** | native |
| % Inhibition | 35.4 | 100.0 | 100.0 | 91.4 | 8.4 | 0.0 | 0.0 |

*JY1119 is an engineered PspA loss mutant and is used in this assay as a negative control
**recom. = recombinant

Having thus described in detail certain preferred embodiments of the present invention, it is to be understood that the invention defined by the appended claims is not to be limited by particular details set forth in the above description, as many apparent variations thereof are possible without departing from the spirit or scope thereof.

REFERENCES

1. Center of Disease Control. 19484. Pneumococcal polysaccharide vaccine usage, United States, MMWR 33: 273–276, 281.
2. Mufson, M. A., G. Oley and D. Hughey, 1982. Pneumococcal disease in a medium-sized community in the United States. JAMA 248: 1486–1489.
3. Hook, E. W., C. A. Horton and D. R. Schaberg. 1983. Failure of intensive care unit support to influence mortality from pneumococcal bacteremia. JAMA 249: 1055–1057.
4. Breiman, R. F., J. S. Spika, V. J. Navarro, P. M. Darden and C. P. Darby. 1990. Pneumococcal bacteremia in Charleston County, South Carolina. Arch. Intern. Med. 150: 1401–1405.
5. Afessa, B., W. L. Greaves and W. R. Frederick. 1995. Pneumococcal bacterimia in adults: a 14-year experience in an inner-city university hospital. Clin. Infec. Diseases 21: 345–351.
6. Fang, G. D., M. Fine, J. Orloff, D. Arisumi, V. L. Yu, W. Kapoor, J. T., Grayston, S. P. Wang, R. Kohler, R. R. Muder and et al. 1990. New and emerging etiologies for community-acquired pneumonia with implications for therapy. A prospective multicenter study of 359 cases. Medicine (Baltimore) 69: 307–316.
7. Marrie, T. J., H. Durant and L. Yates. 1989. Community-acquired pneumonia requiring hospitalization: 5-year prospective study. Rev. Infect. Dis. 11: 586–599.
8. Torres, A., J. Serra-Batlles, A. Ferrer, P. Jimeniz, R. Celis, E. Cobo and R. Rodriquez-Roisin. 1991. Severe community-acquired pneumonia. Epidemiology and prognostic factors. Am Rev Respir Dis. 144: 312–318.
9. Bluestone, C. D., J. S. Stephenson and L. M. Martin. 1992. Ten-year review of otitis media pathogens. Pediatr. Infect. Dis. J. 11: S7–11.
10. Teele, D. W., J. O. Klein, B. Rosner and G. B. O. M. S. Group. 1989. Epidemiology of otitis media during the first seven years of life of chilren in greater Boston: a prospective cohort study. J. Infect. Dis. 160: 83–94.
11. Schutze, G. E., S. L. Kaplan and R. F. Jacobs. 1994. Resistant pneumococcus: A worldwide problem. Infection 22: 233–237.
12. Privitera, G. 1994. Penicillin resistance among *Streptococcus pneumoniae* in Europe. Diagnostic Microbiology and Infectious Disease 19: 157–161.
13. Bizzozero, O. G. Jr. and V. T. Andriole. 1969. Tetracycline-resistant pneumococcal infection. Incidence, clinical presentation and laboratory evaluation. Arch Intern Med. 123: 388–393.
14. Workman, M. R., M. Layton, M. Hussein, J. Philpott-Howard and R. C. George. 1993. Nasal carriage of penicillin-resistant pneumococcus in sickle cell patients (letter). Lancet 342: 746–747.
15. Koornhof, H. J., A. Wasas and K. Klugman. 1992. Antimicrobial resistance in Streptococcus pneumoniae: a South African perspective. Clin. Infect. Dis. 15: 84–94.
16. Dagan, R., P. Yagupsky, A. Goldbart, A. Wasas and K. Klugman. 1994. Increasing prevalence of penicillin-resistant pneumococcal infections in children in southern Israel: implications for future immunization policies. Pediatr. Infect. Dis. J. 13: 782–786.
17. Reichler, M. R., J. Rakovsky, A. Sobotova, M. Slacikova, B. Hlavacova, B. Hill, L. Krajcikova, P. Tarina, R. R. Facklam and R. F. Breiman. 1995. Multiple antimicrobial resistance of pneumococci in children with otitis media, bacteremia, and meningitis in Slovakia. J. Infect. Dis. 171: 1491–1496.
18. Freidland, I. R., S. Shelton, M. Paris, S. Rinderknecht, S. Ehrett, K. Krisher, and G. H. McCracken, Jr., 1993. Dilemmas in diagnosis and management of cephalosporin-resistant *Streptococcus pneumoniae* meningitis. Pediatr. Infect. Dis. J. 12: 196–200.
19. Fedson, D. S., and D. M. Musher. 1994. Pneumococcal Vaccine. In Vaccines. S. A. Plotkin and J. E. A. Montimer, Eds. W. B. Saunders Co., Philidelphia, Pa., p. 517–564.
20. Takala, A. K., J. Eskola, M. Leinonen, H. Kayhty, A. Nissinen, E. Pekkanen and P. H. Makela. 1991. Reduction of oropharyngeal carriage of *Haemophilus influenzae* type b (Hib) in children immunized with an Hib conjugate vaccine. J. Infect. Dis. 164: 982–986.
21. Takala, A. K., M. Santosham, J. Almeido-Hill, M. Wolff, W. Newcomer, R. Reid, H. Kayhty, E. Esko and P. H. Makela. 1993. Vaccination with *Haemophilus influenzae* type b meningococcal protein conjugate vaccine reduces oropharyngeal carriage of *Haemophilus influenzae* type b among American Indian children. Pediatr. Infect. Dis. J. 12: 593–599.
22. Ward, J., J. M. Lieberman and S. L. Cochi. 1994. *Haemophilus influenzae* vaccines. In Vaccines. S. A. Plotkin and J. E. A. Montimer, Eds. W. B. Saunders Co., Philidelphia, Pa., p. 337–386.
23. Murphy, T. V., P. Pastor, F. Medley, M. T. Osterholm, and D. M. Cranoff. 1993. Decreased Haemophilus colonization in children vaccinated with *Haemophilus influenzae* type b conjugate vaccine. J. Pediatr. 122: 517–523.
24. Mohle-Boetani, J. C., G. Ajello, E. Breneman, K. A., Deaver, C. Harvey, B. D. Plikaytis, M. M. Farley, D. S. Stephens and J. D. Wenger. 1993. Carriage of *Haemophilus influenzae* type b in children after widespread vaccination with conjugate *Haemophilus influenzae* type b vaccines. Pediatr. Infect. Dis. J. 12: 589–593.
25. Watson, D. A. and D. M. Musher. 1990. Interruption of capsule production in Streptococcus pneumonia serotype 3 by insertion of transposon Tn916. Infect. Immun. 58: 135–138.
26. Avery, O. T. and R. Dubos. 1931. The protective action of specific enzyme against type III pneumococcus infection in mice. J. Exp. Med. 54: 73–89.
27. Alonso DeVelasco, E., A. F. M. Verheul, J. Verhoef and H. Snippe. 1995. *Streptococcus pneumoniae*: virulence factors, pathogenesis and vaccines. Microbiological Reviews 59: 591–603.
28. Butler, J. C., R. F. Breiman, J. F. Campbell, H.B. Lipman, C. V. Broome and R. R. Facklam. 1993. Pneumococcal polysaccharide vaccine efficacy. An evaluation of current recommendations. JAMA 270: 1826–1831.
29. Hirschmann, J. V., and B. A. Lipsky. 1994. The pneumococcal vaccine after 15 years of use. Arch Intern Med. 154: 373–377.
30. Briles, D. E., J. Yother and L. S. McDaniel. 1988. Role of pneumococcal surface protein A in the virulence of Streptococcus pneumoniae. Rev. Infect. Dis. 10: S372–4.
31. Talkington, D. F., D. C. Voellinger, L. S. McDaniel and D. E. Briles. 1992. Analysis of pneumococcal PspA microheterogeneity in SDS-polyacrylaminde gels and the association of PspA with the cell membrane. Microb. Pathogen. 13: 343–355.
32. Yother, J. and D. E. Briles. 1992. Structural properties and evolutionary relationships of PspA, a surface protein of *Streptococcus pneumoniae*, as revealed by sequence analysis. J. Bacteriol. 174: 601–609.
33. Yother, J. and J. M. White. 1994. Novel surface attachment mechanism of the *Streptococcus pneumoniae* protein PspA. J. Bacteriol. 176: 2976–85.
34. McDaniel, L. S., B. A. Ralph, D. O. McDaniel and D. E. Briles. 1994. Localization of protection-eliciting epitopes of PspA of *Streptococcus pneumoniae* between amino acids residues 192 and 260. Microb. Pathog. 17: 323–337.
35. Ralph, B. A., D. E. Briles and L. S. McDaniel. 1994. Cross-reactive protection eliciting epitopes of pneumoccal surface protein A. Ann N Y Acad. Sci. 730: 361–3.
36.. Waltman, W. D., L. S. McDaniel, B. Andersson, L. Bland, B. M. Gray, C. S. Eden and D. E. Briles. 1988. Protein serotyping of *Streptococcus pneumoniae* based on reactivity to six monoclonal antibodies. Microb. Pathog. 5: 159–67.

What we claim is:

1. A vaccine composition comprising at least two isolated PspAs from S. pneumoniae strains from at least two PspA families.

2. A vaccine composition of claim 1, wherein the at least two families further comprise one or more clades, said clades being defined by one or more S. pneumoniae strains.

3. A vaccine composition of claim 2, where the composition further comprises a minimum of 4 isolated PspAs from S. pneumoniae strains from said one or more clades.

4. A vaccine composition of claim 2, wherein the composition further comprises a maximum of 6 isolated PspAs from S. pneumoniae strains from said one or more clades.

5. A vaccine composition of claim 1, wherein the composition further comprises isolated PspA from S. pneumoniae strain Rx1 (ATCC 55834).

6. A vaccine composition of claim 2, wherein the composition further comprises isolated PspA from S. pneumoniae strain Rx1 (ATCC 55834).

7. A vaccine composition of claim 3, wherein the composition further comprises isolated PspA from S. pneumoniae strain Rx1 (ATCC 55834).

8. A vaccine composition of claim 4, wherein the composition further comprises isolated PspA from S. pneumoniae strain Rx1 (ATCC 55834).

9. A vaccine composition comprising at least two isolated PspAs from S. pneumoniae strains from at least two PspA families having a C-terminal region of an alpha helix of PspA, wherein the C-terminal region comprises an antigenic epitope of interest which elicits a protective immunological response against Streptococcus pneumoniae.

10. A vaccine composition of claim 9, wherein the at least two families further comprise one or more clades, the clades being defined by one or more S. pneumoniae strains.

11. A vaccine composition of claim 10, wherein the composition further comprises a minimum of 4 isolated PspAs from S. pneumoniae strains from the one or more clades.

12. A vaccine composition of claim 10, wherein the composition further comprises a maximum of 6 isolated PspAs from S. pneumoniae strains from the one or more clades.

13. A vaccine composition of claim 9, wherein the composition further comprises isolated PspA from S. pneumoniae strain Rx1 (ATCC 55834).

14. A vaccine composition of claim 10, wherein the composition further comprises isolated PspA from S. pneumoniae strain Rx1 (ATCC 55834).

15. A vaccine composition of claim 11, wherein the composition further comprises isolated PspA from S. pneumoniae strain Rx1 (ATCC 55834).

16. A vaccine composition of claim 12, wherein the composition further comprises isolated PspA from *S. pneumoniae* strain Rx1 (ATCC 55834).

17. A vaccine composition of claim 1, wherein the at least two isolated PspAs are immunologically cross-reactive.

18. A vaccine composition of claim 2, wherein the at least two isolated PspAs are immunologically cross-reactive.

19. A vaccine composition of claim 9, wherein the at least two isolated PspAs are immunologically cross-reactive.

20. A vaccine composition of claim 10, wherein the at least two isolated PspAs are immunologically cross-reactive.

21. A vaccine composition comprising at least two isolated PspAs from at least one PspA family.

22. A vaccine composition of claim 21, wherein the families further comprise one or more clades, said clades being defined by one or more PspAs.

23. A vaccine composition of claim 22, wherein the composition further comprises a minimum of 4 isolated PspAs from one or more clades.

24. A vaccine composition of claim 22, wherein the composition further comprises a maximum of 6 isolated PspAs from the one or more clades.

25. A vaccine composition of claim 21, wherein the composition further comprises isolated PspA from *S. pneumoniae* strain Rx1 (ATCC 55834).

26. A vaccine composition of claim 22, wherein the composition further comprises isolated PspA from *S. pneumoniae* strain Rx1 (ATCC 55834).

27. A vaccine composition of claim 23, wherein the composition further comprises isolated PspA from *S. pneumoniae* strain Rx1 (ATCC 55834).

28. A vaccine composition of claim 24, wherein the composition further comprises isolated PspA from *S. pneumoniae* strain Rx1 (ATCC 55834).

29. A vaccine composition comprising at least two isolated PspAs from at least two PspA families, said families having a C-terminal region of an alpha helix of PspA, wherein the C-terminal region comprises an antigenic epitope of interest which elicits a protective immunological response against *S. pneumoniae*.

30. A vaccine composition of claim 29, wherein the at least two families further comprise one or more clades, the clades being defined by one or more PspAs.

31. A vaccine composition of claim 30, wherein the composition further comprises a minimum of 4 isolated PspAs from the one or more clades.

32. A vaccine composition of claim 30, wherein the composition further comprises a maximum of 6 isolated PspAs from the one or more clades.

33. A vaccine composition of claim 29, wherein the composition further comprises isolated PspA from *S. pneumoniae* strain Rx1 (ATCC 55834).

34. A vaccine composition of claim 30, wherein the composition further comprises isolated PspA from *S. pneumoniae* strain Rx1 (ATCC 55834).

35. A vaccine composition of claim 31, wherein the composition further comprises isolated PspA from *S. pneumoniae* strain Rx1 (ATCC 55834).

36. A vaccine composition of claim 32, wherein the composition further comprises isolated PspA from *S. pneumoniae* strain Rx1 (ATCC 55834).

37. A vaccine composition of claim 21, wherein the at least two isolated PspAs are immunologically cross-reactive.

38. A vaccine composition of claim 22, wherein the at least two isolated PspAs are immunologically cross-reactive.

39. A vaccine composition of claim 29, wherein the at least two isolated PspAs are immunologically cross-reactive.

40. A vaccine composition of claim 30, wherein the at least two isolated PspAs are immunologically cross-reactive.

* * * * *

SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
      (A) LENGTH: 101 amino acids
      (B) TYPE: amino acid
      (C) STRANDEDNESS: Not Relevant
      (D) TOPOLOGY: linear (ii) MOLECULE TYPE: amino acid (xi) SEQUENCE DESCRIPTION: SEQ ID NO:1:

Leu Lys Glu Ile Asp Glu Ser Asp Ser Glu Asp Tyr Val Lys Glu Gly
    1               5                  10                  15

Leu Arg Ala Pro Leu Gln Ser Glu Leu Asp Asp Ala Lys Gln Ala Lys
                    20                  25                  30

Leu Ser Lys Leu Glu Glu Leu Ser Asp Lys Ile Asp Glu Leu Asp Ala
                35                  40                  45

Glu Ile Ala Lys Leu Glu Lys Asn Val Glu Asp Phe Lys Asn Ser Asn
            50                  55                  60

Gly Glu Gln Ala Glu Gln Tyr Arg Ala Ala Ala Glu Glu Asp Leu Ala
    65                  70                  75                  80

Ala Lys Gln Ala Glu Leu Glu Lys Thr Glu Ala Asp Leu Lys Lys Ala
                    85                  90                  95

Val Asn Glu Pro Glu
                    100

(2) INFORMATION FOR SEQ ID NO:2:

(i) SEQUENCE CHARACTERISTICS:
        (A) LENGTH: 101 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:2:

Leu Lys Glu Ile Asp Glu Ser Asp Ser Glu Asp Tyr Val Lys Glu Gly
    1               5                  10                  15

Leu Arg Ala Pro Leu Gln Ser Glu Leu Asp Asp Ala Lys Gln Ala Lys
                    20                  25                  30

Leu Ser Lys Leu Glu Glu Leu Ser Asp Lys Ile Asp Glu Leu Asp Ala
                35                  40                  45

Glu Ile Ala Lys Leu Glu Lys Asn Val Glu Asp Phe Lys Asn Ser Asn
            50                  55                  60

Gly Glu Gln Ala Glu Gln Tyr Arg Ala Ala Ala Gly Glu Asp Leu Ala
    65                  70                  75                  80

Ala Lys Gln Ala Glu Leu Glu Lys Thr Glu Ala Asp Leu Lys Lys Ala
                    85                  90                  95

Val Asn Glu Pro Glu
                    100

(2) INFORMATION FOR SEQ ID NO:3:

(i) SEQUENCE CHARACTERISTICS:
        (A) LENGTH: 101 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:3:

Leu Lys Glu Ile Asp Glu Ser Asp Ser Glu Asp Tyr Val Lys Glu Gly
    1               5                  10                  15

Glu Arg Ala Pro Leu Gln Ser Glu Leu Asp Asp Ala Lys Gln Ala Lys
                    20                  25                  30

Leu Ser Lys Leu Glu Glu Leu Ser Asp Lys Ile Asp Glu Leu Asp Ala
                35                  40                  45

```
        Glu Ile Ala Lys Leu Glu Lys Asp Val Glu Asp Phe Lys Asn Ser Asp
         50                  55                  60

Gly Glu Gln Ala Gly Gln Tyr Leu Ala Ala Gly Glu Asp Leu Ile
        65                  70                  75                  80

Ala Lys Lys Ala Glu Leu Glu Lys Ala Glu Ala Asp Leu Lys Lys Ala
                         85                  90                  95

Val Asp Glu Pro Glu
                        100

(2) INFORMATION FOR SEQ ID NO:4:

(i) SEQUENCE CHARACTERISTICS:
        (A) LENGTH: 101 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:4:

Leu Lys Glu Ile Asp Glu Ser Asp Ser Glu Asp Tyr Val Lys Glu Gly
        1               5                  10                  15

Glu Arg Ala Pro Leu Gln Ser Glu Leu Asp Asp Ala Lys Gln Ala Lys
                        20                  25                  30

Leu Ser Lys Leu Glu Glu Leu Ser Asp Lys Ile Asp Glu Leu Asp Ala
                       35                  40                  45

Glu Ile Ala Lys Leu Glu Lys Asp Val Glu Asp Phe Lys Asn Ser Asp
        50                  55                  60

Gly Glu Gln Ala Gly Gln Tyr Leu Ala Ala Ala Glu Glu Asp Leu Ile
       65                  70                  75                  80

Ala Lys Lys Ala Glu Leu Glu Gln Thr Glu Ala Asp Leu Lys Lys Ala
                        85                  90                  95

Val Asn Glu Pro Glu
                       100

(2) INFORMATION FOR SEQ ID NO:5:

(i) SEQUENCE CHARACTERISTICS:
        (A) LENGTH: 101 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:5:

Leu Lys Glu Ile Asp Glu Ser Asp Ser Glu Asp Tyr Val Lys Glu Gly
        1               5                  10                  15

Glu Arg Ala Pro Leu Gln Ser Glu Leu Asp Asp Ala Lys Gln Ala Lys
                        20                  25                  30

Leu Ser Lys Leu Glu Glu Xaa Ser Asp Lys Xaa Asp Glu Leu Asp Ala
                       35                  40                  45

Glu Ile Ala Lys Leu Glu Lys Asp Val Glu Asp Phe Lys Asn Ser Asp
        50                  55                  60

Gly Glu Gln Ala Gly Gln Tyr Leu Ala Ala Ala Glu Glu Asp Leu Ile
       65                  70                  75                  80

Ala Lys Lys Ala Xaa Leu Glu Lys Ala Glu Ala Asp Leu Lys Lys Ala
                        85                  90                  95

Val Asp Glu Pro Glu
                       100
```

(2) INFORMATION FOR SEQ ID NO:6:

(i) SEQUENCE CHARACTERISTICS:
        (A) LENGTH: 101 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:6:

```
Leu Lys Glu Ile Asp Glu Ser Asp Ser Glu Asp Tyr Ile Lys Glu Gly
 1               5                  10                  15

Glu Arg Ala Pro Leu Gln Ser Lys Leu Asp Asp Ala Lys Lys Ala Lys
            20                  25                  30

Leu Ser Lys Leu Asp Glu Xaa Ser Asp Lys Xaa Asp Glu Leu Asp Ala
        35                  40                  45

Glu Ile Ala Lys Leu Glu Lys Asp Val Gly Asp Phe Pro Asn Ser Asp
    50                  55                  60

Gly Glu Gln Ala Gly Gln Tyr Leu Val Ala Ala Glu Lys Asp Leu Asp
65                  70                  75                  80

Ala Lys Glu Ala Glu Leu Gly Asn Thr Gly Ala Asp Leu Lys Lys Ala
            85                  90                  95

Val Asp Glu Pro Glu
            100
```

(2) INFORMATION FOR SEQ ID NO:7:

(i) SEQUENCE CHARACTERISTICS:
        (A) LENGTH: 101 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:7:

```
Leu Lys Gly Ile Asp Glu Ser Asp Ser Glu Asp Tyr Val Lys Glu Gly
 1               5                  10                  15

Leu Arg Ala Pro Leu Gln Ser Glu Leu Asp Asp Ala Lys Gln Arg Thr
            20                  25                  30

Leu Ser Thr Leu Glu Glu Leu Ser Asp Lys Ile Asp Glu Leu Asp Ala
        35                  40                  45

Glu Ile Ala Lys Leu Glu Lys Asn Val Glu Tyr Phe Lys Lys Thr Asp
    50                  55                  60

Ala Glu Gln Thr Glu Gln Tyr Leu Ala Ala Ala Glu Lys Asp Leu Ala
65                  70                  75                  80

Asp Lys Lys Ala Glu Leu Glu Lys Thr Glu Ala Asp Leu Lys Lys Ala
            85                  90                  95

Val Asn Glu Pro Glu
            100
```

(2) INFORMATION FOR SEQ ID NO:8:

(i) SEQUENCE CHARACTERISTICS:
        (A) LENGTH: 102 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:8:

```
Leu Lys Glu Ile Asp Glu Ser Asp Ser Glu Asp Tyr Val Lys Glu Gly
1               5                   10                  15

Leu Arg Val Pro Leu Gln Ser Glu Leu Asp Asp Val Lys Gln Ala Lys
                20                  25                  30

Leu Leu Lys Leu Glu Glu Leu Ser Asp Lys Ile Asp Glu Leu Asp Ala
            35                  40                  45

Glu Ile Ala Lys Asn Leu Lys Lys Asp Val Glu Asp Phe Gln Asn Ser
        50                  55                  60

Gly Gly Gly Tyr Ser Ala Leu Tyr Leu Glu Ala Ala Gly Lys Asp Leu
65                  70                  75                  80

Val Ala Lys Lys Ala Glu Leu Glu Lys Thr Glu Ala Asp Leu Lys Lys
                85                  90                  95

Ala Val Asn Glu Pro Glu
            100
```

(2) INFORMATION FOR SEQ ID NO:9:

(i) SEQUENCE CHARACTERISTICS:
        (A) LENGTH: 99 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:9:

```
Leu Lys Glu Ile Asp Glu Ser Asp Ser Glu Asp Tyr Val Lys Glu Gly
1               5                   10                  15

Leu Arg Ala Pro Leu Gln Ser Glu Leu Asp Asp Ala Lys Gln Ala Lys
                20                  25                  30

Leu Ser Lys Leu Glu Glu Leu Ser Asp Lys Ile Asp Glu Leu Asp Ala
            35                  40                  45

Glu Ile Ala Lys Leu Glu Lys Asp Val Glu Asp Phe Lys Asn Ser Asp
        50                  55                  60

Gly Glu Gln Ala Gln Tyr Leu Ala Ala Ala Glu Glu Asp Leu Ala Lys
65                  70                  75                  80

Lys Ala Glu Leu Glu Lys Thr Glu Ala Asp Leu Lys Lys Ala Val Asn
                85                  90                  95

Glu Pro Glu
```

(2) INFORMATION FOR SEQ ID NO:10:

(i) SEQUENCE CHARACTERISTICS:
        (A) LENGTH: 99 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:10:

```
Leu Lys Glu Ile Asp Glu Ser Asp Ser Glu Asp Tyr Val Lys Glu Gly
1               5                   10                  15

Phe Arg Ala Pro Leu Gln Ser Glu Leu Asp Ala Lys Gln Ala Lys Leu
                20                  25                  30

Ser Lys Leu Glu Glu Leu Ser Asp Lys Ile Asp Glu Leu Asp Ala Glu
            35                  40                  45

Ile Ala Lys Leu Glu Asp Gln Leu Lys Ala Ala Glu Glu Asn Asn Asn
        50                  55                  60
```

```
Val Glu Asp Tyr Phe Lys Glu Gly Leu Glu Lys Thr Ile Ala Ala Lys
 65                  70                  75                  80

Lys Ala Glu Leu Glu Lys Thr Glu Ala Asp Leu Lys Lys Ala Val Asn
                 85                  90                  95

Glu Pro Glu
```

(2) INFORMATION FOR SEQ ID NO:11:

(i) SEQUENCE CHARACTERISTICS:
        (A) LENGTH: 99 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:11:

```
Leu Lys Glu Ile Asp Glu Ser Glu Ser Glu Asp Tyr Ala Lys Glu Gly
 1               5                  10                  15

Phe Arg Ala Pro Leu Gln Ser Lys Leu Asp Ala Lys Lys Ala Lys Leu
                 20                  25                  30

Ser Lys Leu Glu Glu Leu Ser Asp Lys Ile Asp Glu Leu Asp Ala Glu
                 35                  40                  45

Ile Ala Lys Leu Glu Asp Gln Leu Lys Ala Ala Glu Glu Asn Asn Asn
 50                  55                  60

Val Glu Asp Tyr Phe Lys Glu Gly Leu Glu Lys Thr Ile Ala Ala Lys
 65                  70                  75                  80

Lys Ala Glu Leu Glu Lys Thr Glu Ala Asp Leu Lys Lys Ala Val Asn
                 85                  90                  95

Glu Pro Glu
```

(2) INFORMATION FOR SEQ ID NO:12:

(i) SEQUENCE CHARACTERISTICS:
        (A) LENGTH: 99 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:12:

```
Leu Lys Glu Ile Asp Glu Ser Glu Ser Glu Asp Tyr Ala Lys Glu Gly
 1               5                  10                  15

Phe Arg Ala Pro Leu His Ser Lys Leu Asp Ala Lys Lys Ala Lys Leu
                 20                  25                  30

Ser Lys Leu Glu Glu Leu Ser Asp Lys Ile Asp Glu Leu Asp Ala Glu
                 35                  40                  45

Ile Ala Lys Leu Glu Asp Gln Leu Lys Ala Val Glu Glu Asn Asn Asn
 50                  55                  60

Val Glu Asp Tyr Ser Thr Glu Gly Leu Glu Lys Thr Ile Ala Ala Lys
 65                  70                  75                  80

Lys Thr Glu Leu Glu Lys Thr Glu Ala Asp Leu Lys Lys Ala Val Asn
                 85                  90                  95

Glu Pro Glu
```

(2) INFORMATION FOR SEQ ID NO:13:

(i) SEQUENCE CHARACTERISTICS:
        (A) LENGTH: 99 amino acids
        (B) TYPE: amino acid (C) STRANDEDNESS: Not Relevant
        (D) TOPOLOGY: linear (ii) MOLECULE TYPE: amino acid (xi) SEQUENCE DESCRIPTION: SEQ ID NO:13:

Leu Lys Asp Ile Asp Glu Ser Asp Ser Glu Asp Tyr Ala Lys Glu Gly
    1               5                   10                  15

Leu Arg Ala Pro Leu Gln Ser Glu Leu Asp Thr Lys Lys Ala Lys Leu
                20                  25                  30

Leu Lys Leu Glu Glu Leu Ser Gly Lys Ile Glu Glu Leu Asp Ala Glu
            35                  40                  45

Ile Xaa Glu Leu Glu Val Gln Leu Lys Asp Val Glu Gly Asn Asn Asn
        50                  55                  60

Val Glu Ala Tyr Phe Lys Gly Leu Glu Lys Thr Thr Ala Glu Lys
    65                  70                  75                  80

Ala Thr Glu Leu Glu Lys Ala Glu Ala Asp Leu Lys Lys Ala Val Asp
                85                  90                  95

Glu Pro Glu (2) INFORMATION FOR SEQ ID NO:14:

(i) SEQUENCE CHARACTERISTICS:
        (A) LENGTH: 99 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:14:

Leu Glu Glu Ile Asn Glu Ser Asp Ser Glu Asp Tyr Ala Lys Glu Gly
    1               5                   10                  15

Phe Arg Ala Pro Leu Gln Ser Lys Leu Asp Ala Lys Lys Ala Lys Leu
                20                  25                  30

Leu Lys Leu Glu Glu Leu Ser Gly Lys Ile Glu Glu Leu Asp Ala Glu
            35                  40                  45

Ile Ala Glu Leu Glu Val Gln Leu Lys Asp Val Glu Gly Asn Asn Asn
        50                  55                  60

Val Glu Ala Tyr Phe Lys Gly Leu Glu Lys Thr Thr Ala Glu Lys
    65                  70                  75                  80

Ala Thr Glu Leu Glu Lys Ala Glu Ala Asp Leu Lys Lys Ala Val Asp
                85                  90                  95

Glu Pro Glu (2) INFORMATION FOR SEQ ID NO:15:

(i) SEQUENCE CHARACTERISTICS:
        (A) LENGTH: 99 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:15:

Leu Lys Glu Ile Asp Glu Ser Asp Ser Glu Asp Tyr Leu Lys Glu Gly
    1               5                   10                  15

Leu Arg Ala Pro Leu Gln Ser Lys Leu Asp Thr Lys Lys Ala Lys Leu
                20                  25                  30

Ser Lys Leu Glu Glu Leu Ser Asp Lys Ile Asp Glu Leu Asp Ala Glu

```
                  35                   40                   45

Ile Ala Lys Leu Glu Val Gln Leu Lys Asp Val Glu Gly Asn Asn Asn
                  50                   55                   60

Val Glu Ala Tyr Phe Lys Glu Gly Leu Glu Lys Thr Thr Ala Glu Lys
         65                   70                   75                   80

Ala Thr Glu Leu Glu Lys Ala Glu Ala Asp Leu Lys Lys Ala Val Asp
                           85                   90                   95

Glu Pro Glu (2) INFORMATION FOR SEQ ID NO:16:

(i) SEQUENCE CHARACTERISTICS:
        (A) LENGTH: 99 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:16:

Pro Lys Arg Ile Met Ser Leu Ser Gln Lys Val Xaa Leu Lys Xaa Val
         1               5                   10                  15

Cys Arg Ala Pro Leu Gln Ser Lys Leu Asp Ala Gln Lys Ala Glu Leu
                           20                  25                  30

Leu Lys Leu Glu Glu Leu Ser Gly Lys Ile Glu Glu Leu Asp Ala Glu
                           35                  40                  45

Ile Ala Glu Leu Glu Val Gln Leu Lys Asp Val Glu Gly Asn Asn Asn
                  50                   55                   60

Val Glu Ala Tyr Phe Lys Glu Gly Leu Glu Lys Thr Thr Ala Glu Lys
         65                   70                   75                   80

Ala Thr Glu Leu Glu Xaa Ala Xaa Ala Asp Leu Lys Lys Ala Val Asp
                           85                   90                   95

Glu Pro Glu (2) INFORMATION FOR SEQ ID NO:17:

(i) SEQUENCE CHARACTERISTICS:
        (A) LENGTH: 99 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:17:

Leu Lys Glu Ile Asp Glu Ser Asp Ser Glu Asp Tyr Ala Lys Glu Gly
         1               5                   10                  15

Phe Arg Ala Pro Leu Gln Ser Lys Leu Asp Ala Lys Lys Ala Lys Leu
                           20                  25                  30

Ser Lys Leu Glu Glu Leu Ser Asp Lys Ile Asp Glu Leu Asp Ala Glu
                           35                  40                  45

Ile Ala Lys Leu Glu Val Gln Leu Lys Asp Ala Glu Gly Asn Asn Asn
                  50                   55                   60

Val Glu Ala Tyr Phe Lys Glu Gly Leu Glu Lys Thr Thr Ala Glu Lys
         65                   70                   75                   80

Ala Thr Glu Leu Glu Lys Ala Glu Ala Asp Leu Lys Lys Ala Val Asp
                           85                   90                   95

Glu Pro Glu
```

(2) INFORMATION FOR SEQ ID NO:18:

(i) SEQUENCE CHARACTERISTICS:
        (A) LENGTH: 80 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:18:

```
Leu Asp Lys Glu Ala Gly Glu Ala Glu Leu Asp Lys Lys Ala Asp Gly
  1               5                  10                  15

Leu Pro Asn Lys Val Ser Asp Leu Glu Lys Glu Ile Ser Asn Leu Glu
                 20                  25                  30

Ile Leu Leu Gly Gly Ala Asp Ser Glu Asp Thr Ala Ala Leu Pro
             35                  40                  45

Asn Lys Leu Ala Thr Lys Lys Ala Glu Leu Glu Lys Thr Gln Lys Glu
             50                  55                  60

Leu Asp Ala Ala Leu Asn Glu Leu Gly Pro Asp Gly Asp Glu Glu Glu
 65                  70                  75                  80
```

(2) INFORMATION FOR SEQ ID NO:19:

(i) SEQUENCE CHARACTERISTICS:
        (A) LENGTH: 104 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:19:

```
Leu Ala Lys Lys Gln Thr Glu Leu Glu Lys Leu Leu Asp Ser Leu Asp
  1               5                  10                  15

Pro Glu Gly Lys Thr Gln Asp Glu Leu Asp Lys Glu Ala Glu Glu Ala
                 20                  25                  30

Glu Leu Asp Lys Lys Ala Asp Glu Leu Pro Asn Lys Val Ala Asp Leu
             35                  40                  45

Glu Lys Glu Ile Ser Asn Leu Glu Ile Leu Leu Gly Gly Ala Asp Ser
             50                  55                  60

Glu Asp Asp Thr Ala Ala Leu Pro Asn Lys Leu Ala Thr Lys Lys Ala
 65                  70                  75                  80

Glu Leu Glu Lys Thr Gln Lys Glu Leu Asp Ala Ala Leu Asn Glu Leu
                 85                  90                  95

Gly Pro Asp Gly Asp Glu Glu Glu
                100
```

(2) INFORMATION FOR SEQ ID NO:20:

(i) SEQUENCE CHARACTERISTICS:
        (A) LENGTH: 104 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:20:

```
Leu Ala Lys Lys Gln Thr Glu Leu Glu Lys Leu Leu Asp Asn Leu Asp
  1               5                  10                  15

Pro Glu Gly Lys Thr Gln Asp Glu Leu Asp Lys Glu Ala Ala Glu Ala
                 20                  25                  30
```

```
Glu Leu Asp Lys Lys Ala Asp Glu Leu Pro Asn Lys Val Ala Asp Leu
         35                  40                  45

Glu Lys Glu Ile Ser Asn Leu Glu Ile Leu Leu Gly Gly Ala Asp Pro
 50                  55                  60

Glu Asp Asp Thr Ala Ala Leu Pro Asn Lys Leu Ala Thr Lys Lys Ala
 65                  70                  75                  80

Glu Leu Glu Lys Thr Pro Lys Glu Leu Asp Ala Ala Leu Asn Glu Leu
             85                  90                  95

Gly Pro Asp Gly Asp Glu Glu Glu
                100
```

(2) INFORMATION FOR SEQ ID NO:21:

(i) SEQUENCE CHARACTERISTICS:
       (A) LENGTH: 102 amino acids
       (B) TYPE: amino acid
       (C) STRANDEDNESS: Not Relevant
       (D) TOPOLOGY: linear (ii) MOLECULE TYPE: amino acid (xi) SEQUENCE DESCRIPTION: SEQ ID NO:21:

```
Leu Ala Lys Lys Gln Thr Glu Leu Glu Lys Leu Leu Asp Leu Asp Pro
 1               5                  10                  15

Glu Gly Lys Thr Gln Asp Glu Leu Asp Lys Glu Ala Glu Ala Glu Leu
             20                  25                  30

Asp Lys Lys Ala Asp Glu Leu Pro Asn Lys Val Ala Asp Leu Glu Lys
         35                  40                  45

Glu Ile Ser Asn Leu Glu Ile Leu Leu Gly Gly Ala Asp Ser Glu Asp
 50                  55                  60

Asp Thr Ala Ala Leu Pro Asn Lys Leu Ala Thr Lys Lys Ala Glu Leu
 65                  70                  75                  80

Glu Lys Thr Gln Lys Glu Leu Asp Ala Ala Leu Asn Glu Leu Gly Pro
             85                  90                  95

Asp Gly Asp Glu Glu Glu
                100
```

(2) INFORMATION FOR SEQ ID NO:22:

(i) SEQUENCE CHARACTERISTICS:
       (A) LENGTH: 108 amino acids
       (B) TYPE: amino acid
       (C) STRANDEDNESS: Not Relevant
       (D) TOPOLOGY: linear (ii) MOLECULE TYPE: amino acid (xi) SEQUENCE DESCRIPTION: SEQ ID NO:22:

```
Leu Glu Lys Ala Gly Ala Gly Leu Gly Asn Leu Leu Ser Thr Leu Asp
 1               5                  10                  15

Pro Glu Gly Lys Thr Gln Asp Glu Leu Asp Lys Glu Ala Ala Glu Ala
             20                  25                  30

Glu Leu Asn Lys Lys Val Glu Ala Leu Pro Asn Gln Val Ser Glu Leu
         35                  40                  45

Glu Glu Glu Leu Ser Lys Leu Glu Asp Asn Leu Lys Asp Ala Glu Thr
 50                  55                  60

Asn His Val Glu Asp Tyr Ile Lys Gly Leu Glu Glu Ala Ile Ala
 65                  70                  75                  80

Thr Lys Gln Ala Glu Leu Glu Lys Thr Pro Lys Glu Leu Asp Ala Ala
             85                  90                  95
```

-continued

```
Leu Asn Glu Leu Gly Pro Asp Gly Asp Glu Glu Glu
        100                 105
```

(2) INFORMATION FOR SEQ ID NO:23:

(i) SEQUENCE CHARACTERISTICS:
        (A) LENGTH: 108 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:23:

```
Leu Glu Lys Ala Gly Ala Gly Leu Gly Asn Leu Leu Ser Thr Leu Asp
1               5                   10                  15

Pro Glu Gly Lys Thr Gln Asp Glu Leu Asp Lys Glu Ala Ala Glu Ala
            20                  25                  30

Glu Leu Asn Lys Lys Val Glu Ala Leu Pro Asn Gln Val Ser Glu Leu
        35                  40                  45

Glu Glu Glu Leu Ser Lys Leu Glu Asp Asn Leu Lys Asp Ala Glu Thr
50                  55                  60

Asn His Val Glu Asp Tyr Ile Lys Glu Gly Leu Glu Glu Ala Ile Ala
65                  70                  75                  80

Thr Lys Gln Ala Glu Leu Glu Lys Thr Pro Lys Glu Leu Asp Ala Ala
            85                  90                  95

Leu Asn Glu Leu Gly Pro Asp Gly Asp Glu Glu Glu
        100                 105
```

(2) INFORMATION FOR SEQ ID NO:24:

(i) SEQUENCE CHARACTERISTICS:
        (A) LENGTH: 108 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:24:

```
Leu Glu Asp Ala Glu Leu Glu Leu Glu Lys Val Leu Ala Thr Leu Asp
1               5                   10                  15

Pro Glu Gly Lys Thr Gln Asp Glu Leu Asp Lys Glu Ala Ala Glu Ala
            20                  25                  30

Glu Leu Asn Glu Lys Val Glu Ala Leu Gln Asn Gln Val Ala Glu Leu
        35                  40                  45

Glu Glu Glu Leu Ser Lys Leu Glu Asp Asn Leu Lys Asp Ala Glu Thr
50                  55                  60

Asn Asn Val Glu Asp Tyr Ile Lys Glu Gly Leu Glu Glu Ala Ile Ala
65                  70                  75                  80

Thr Lys Lys Ala Glu Leu Glu Lys Thr Gln Lys Glu Leu Asp Ala Ala
            85                  90                  95

Leu Asn Glu Leu Gly Pro Asp Gly Asp Glu Glu Glu
        100                 105
```

(2) INFORMATION FOR SEQ ID NO:25:

(i) SEQUENCE CHARACTERISTICS:
        (A) LENGTH: 108 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:25:

```
Leu Glu Lys Ala Glu Ala Glu Leu Glu Asn Leu Leu Ser Thr Leu Asp
  1               5                  10                  15

Pro Gly Gly Lys Thr Gln Asp Glu Leu Asp Lys Gly Ala Ala Glu Ala
               20                  25                  30

Glu Leu Asn Lys Lys Val Glu Ala Leu Pro Asn Pro Val Xaa Glu Leu
           35                  40                  45

Glu Glu Glu Leu Ser Pro Pro Glu Asp Asn Leu Lys Asp Ala Glu Thr
       50                  55                  60

Asn His Val Glu Asp Tyr Ile Lys Glu Gly Leu Glu Glu Ala Ile Ala
 65                  70                  75                  80

Thr Lys Gln Ala Glu Leu Glu Thr Pro Gln Glu Val Asp Ala Ala
               85                  90                  95

Leu Asn Asp Leu Val Pro Asp Gly Gly Glu Glu Glu
              100                 105
```

(2) INFORMATION FOR SEQ ID NO:26:

(i) SEQUENCE CHARACTERISTICS:
    (A) LENGTH: 108 amino acids
    (B) TYPE: amino acid
    (C) STRANDEDNESS: Not Relevant
    (D) TOPOLOGY: linear (ii) MOLECULE TYPE: amino acid (xi) SEQUENCE DESCRIPTION: SEQ ID NO:26:

```
Leu Glu Lys Ala Glu Ala Glu Leu Glu Asn Leu Leu Ser Thr Leu Asp
  1               5                  10                  15

Pro Glu Gly Lys Thr Gln Asp Glu Leu Asp Lys Glu Ala Ala Glu Ala
               20                  25                  30

Glu Leu Asn Lys Lys Val Glu Ala Leu Pro Asn Gln Val Ser Glu Leu
           35                  40                  45

Glu Glu Glu Leu Ser Lys Leu Glu Asp Asn Leu Lys Asp Ala Glu Thr
       50                  55                  60

Asn Asn Val Glu Asp Tyr Ile Lys Glu Gly Leu Glu Glu Ala Ile Ala
 65                  70                  75                  80

Thr Lys Gln Ala Glu Leu Glu Lys Thr Pro Lys Glu Leu Asp Ala Ala
               85                  90                  95

Leu Asn Glu Leu Gly Pro Asp Gly Asp Glu Glu Glu
              100                 105
```

(2) INFORMATION FOR SEQ ID NO:27:

(i) SEQUENCE CHARACTERISTICS:
    (A) LENGTH: 119 amino acids
    (B) TYPE: amino acid
    (C) STRANDEDNESS: Not Relevant
    (D) TOPOLOGY: linear (ii) MOLECULE TYPE: amino acid (xi) SEQUENCE DESCRIPTION: SEQ ID NO:27:

```
Leu Glu Asp Ser Gly Leu Gly Leu Glu Lys Val Leu Ala Thr Leu Asp
  1               5                  10                  15

Pro Gly Gly Glu Thr Pro Asp Gly Leu Asp Lys Glu Ala Ser Glu Asp
               20                  25                  30

Ser Asn Ile Gly Ala Leu Pro Asn Gln Val Ser Asp Leu Glu Asn Gln
           35                  40                  45
```

-continued

```
Val Ser Glu Leu Asp Arg Glu Val Thr Arg Leu Pro Ser Asp Leu Lys
    50                  55                  60

Asp Thr Glu Gly Asn Asn Val Gly Asp Tyr Val Lys Gly Gly Leu Glu
65                  70                  75                  80

Lys Ala Leu Thr Asp Glu Lys Val Gly Leu Asn Asn Thr Pro Lys Ala
                85                  90                  95

Leu Asp Thr Ala Pro Lys Ala Leu Asp Thr Ala Leu Asn Glu Leu Gly
                100                 105                 110

Pro Asp Gly Asp Glu Glu Glu
            115
```

(2) INFORMATION FOR SEQ ID NO:28:

(i) SEQUENCE CHARACTERISTICS:
        (A) LENGTH: 96 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:28:

```
Gln Ala Leu Tyr Glu Ser Thr Gln Glu Gln Ile Glu Glu Leu Lys Asp
1               5                   10                  15

Tyr Asn Glu Gln Ile Ser Glu Gly Glu Glu Thr Leu Ile Leu Ala Ile
                20                  25                  30

Gln Asn Lys Ile Ser Asp Leu Asp Asp Lys Ile Ala Glu Ala Glu Lys
                35                  40                  45

Lys Leu Ala Asp Ser Gln Asn Gly Glu Gly Val Glu Asp Tyr Trp Thr
    50                  55                  60

Ser Gly Asp Glu Asp Lys Leu Glu Lys Leu Gln Ala Glu Gln Asp Glu
65                  70                  75                  80

Leu Gln Ala Glu Leu Asp Gln Leu Leu Asp Glu Val Asp Gly Gln Glu
                85                  90                  95
```